US005643747A

United States Patent [19]
Baker et al.

[11] Patent Number: 5,643,747
[45] Date of Patent: Jul. 1, 1997

[54] **GENES FOR THE EXPORT OF *PERTUSSIS* HOLOTOXIN**

[75] Inventors: Steven M. Baker; Robert A. Deich, both of Rochester, N.Y.

[73] Assignee: American Cyanamid Company, Parsippany, N.J.

[21] Appl. No.: 221,750

[22] Filed: Mar. 31, 1994

Related U.S. Application Data

[63] Continuation-in-part of Ser. No. 31,619, Mar. 15, 1993, abandoned.

[51] Int. Cl.$^6$ .......................... C12N 15/31; C12N 15/74; C12N 1/21; C07H 21/04
[52] U.S. Cl. ................ 435/69.1; 435/252.3; 435/252.33; 435/320.1; 536/23.7
[58] Field of Search ........................... 435/69.1, 69.7, 435/252.3, 252.33, 320.1; 536/23.7

[56] References Cited

U.S. PATENT DOCUMENTS 5,380,653  1/1995  Palva ....................................... 435/69.7

FOREIGN PATENT DOCUMENTS 0232229  8/1987  European Pat. Off. .

OTHER PUBLICATIONS

Arico et al. (1987) "*Bordetella parapertussis* and *Bordetella bronchiseptica* contain transcriptionally silent *pertussis* toxin genes" J. Bacteriol. 169:2847–2853.

Johnson et al. (1994) "Detection and subcellular localization of three Ptl proteins involved in the secretion of *pertussis* toxin from *B. pertussis*" J. Bacteriol. 176:5350–56.

A Covacci and R. Rappuoli, "*pertussis* Toxin Export Requires Accessory Genes Located Downstream From The *pertussis* Toxin Operon", *Molecular Microbiology* 8(3):429–434, (1993).

Nicosia, A. et al. *Proc. Natl. Acad. Sci. USA* 83:4631–4635 (1986). "Cloning and Sequencing of the *pertussis* Toxin Genes: Operon Structure and Gene Duplication".

Lee, C.K. et al. *Infect. Immun.* 57:1413–1418 (1989). "Expression of *pertussis* Toxin in Bordetella *Bordetella bronchiseptica* and *Bordetella parapertussis* Carrying Recombinant Plasmids".

Burnett, W.N. et al., "Direct Expression of *Bordetella pertussis* Toxin Subunits to High levels in *Escherichia coli*", *Bio/Technology* 6:699–705 (1988).

Locht, C. and J. M. Keith, *Science* 232:1258–1264 (1986). "*pertussis* Toxin Gene: Nucleotide Sequence and Genetic Organization".

He, et al., *Proc. Natl. Acad. Sci. USA* 88:1079–1083 (1991). "Cloned Erwinia Chrysanthemi Out Genes Enable *Escherichia coli* to Selectively Secrete a Diverse Family Heterologous Proteins to its Milieu".

Pugsley, A.P., *Proc. Natl. Acad. Sci. USA* 89:12058–12062 (1992). "Translocation of a Folded Protein Across the Outer Membrane in *Escherichia coli*".

Pugsley, A.P., *Microbiology Review*, 57:50–108 (1993). "The Complete Secretory Pathway in Gram–Negative Bacteria".

Stibitz, et al., "Derivation of a Physical Map of the Chromosome of *Bordetella pertussis* Tohama I", *Journal of Bacterilogy*, 174:7770–7777 (1992).

Weiss et al., "Use of the Promoter Fusion Transposon Tn5 1ac To Identify Mutations in *Bordetella pertussis vir*–Regulated Genes", *Infection and Immunity*, 57:2674–2682 (1989).

Shirasu, et al., "The *vir*B Operon of the *Agrobacterium tumefaciens* Virulence Regulon has Sequence ...", *Nucleic Acids Research*, 21:353–354 (1993).

Weiss, et al., "Molecular Characterization of an Operon Required for *pertussis* Toxin Secretion", *Proc. Natl. Acad. Sci.*, 90:2970–2974 (1993).

Johnson, et al., Abstracts of the 92nd General Meeting of the American Society for Microbiology, p.29, Abstract B–15 (1992).

*Primary Examiner*—Jasemine C. Chambers
*Assistant Examiner*—Scott D. Priebe
*Attorney, Agent, or Firm*—Hamilton, Brook, Smith & Reynolds, P.C.

[57] ABSTRACT

The invention relates to a cloned region of the *Bordetella pertussis* genome located 3' of the ptx operon encoding factors required for expression, assembly and secretion of pertussis holotoxin. Methods for obtaining increased levels of holotoxin production using homologous and heterologous hosts are also described.

18 Claims, 3 Drawing Sheets

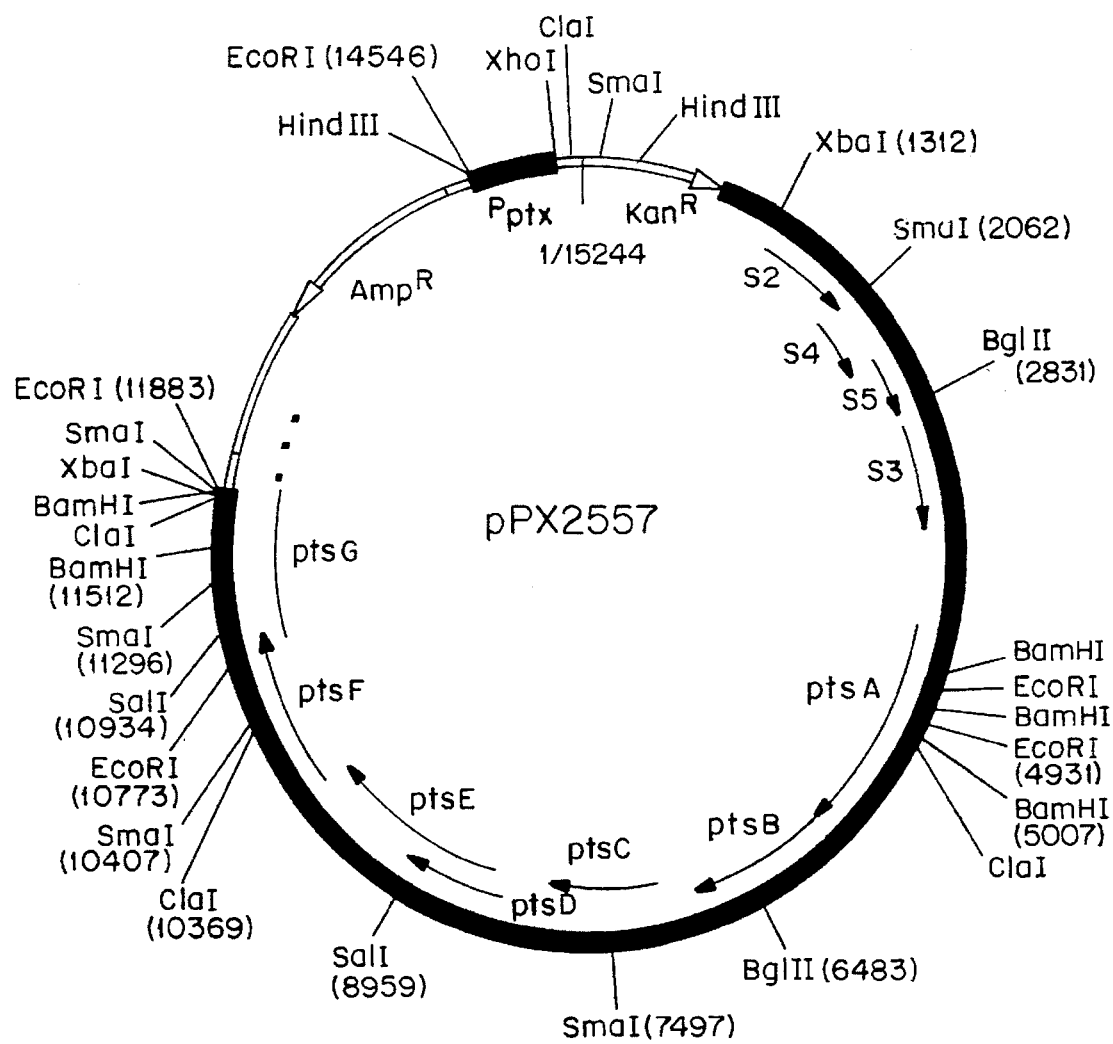
FIG. I

Strains
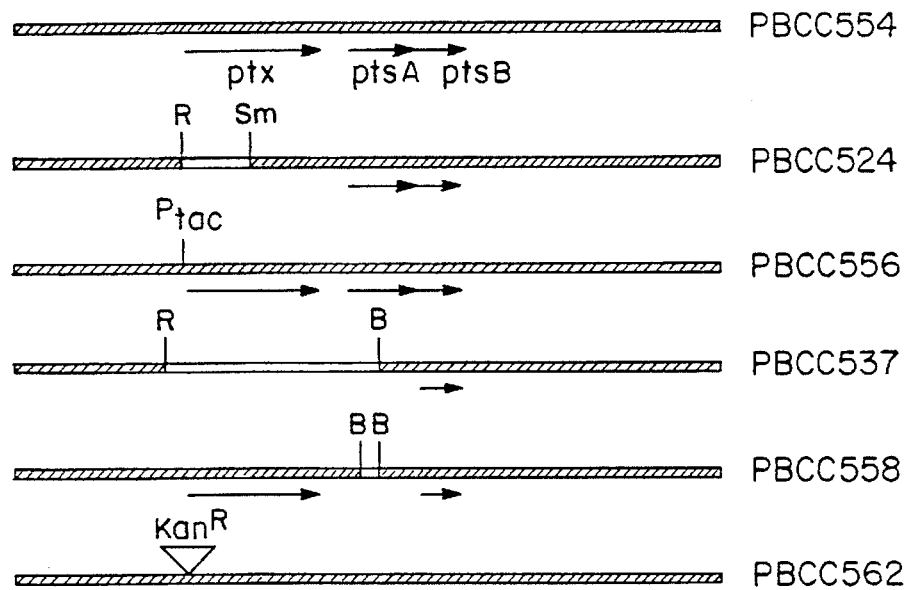
Plasmids
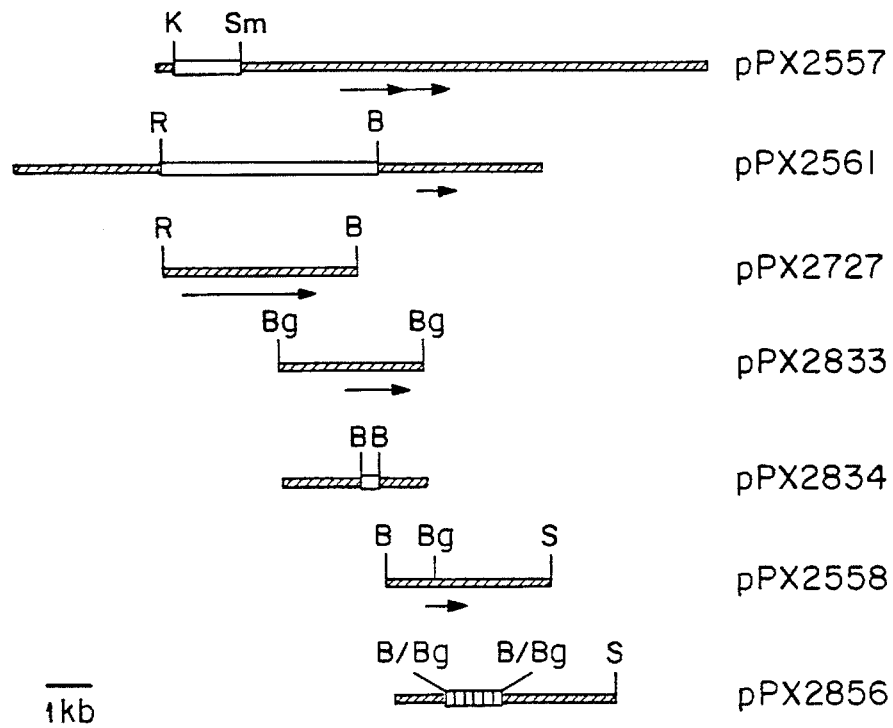
FIG. 3

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 7742 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| ATGAACCGGC | GCGGCGGCCA | GACCGCATTT | GCGGCCATTG | CGCGCAACGA | GCGCGCCATC | 60 |
| GCTGCGTTCA | TCCCCTACAG | CAGCCACCTG | ACGGACACGA | CGCTGATCAC | CCATGGCGCG | 120 |
| GACCTGGTCC | GCACCTGGCG | CGTACAGGGG | ATCGCCTTCG | AAAGCGCCGA | GCCAGAGCTG | 180 |
| GTTTCGCAGC | GCCATGAACA | GCTCAACGGC | CTGTGGCGCG | CCATCTCGTG | CGAGCAGGTC | 240 |
| GCGCTTTGGA | TCCATTGCAT | CCGGCGCAAG | ACGCAGGCCG | GGTTGGATGC | GCGGTACGAA | 300 |
| AATCCGTTCT | GCCGCGCGCT | CGACGCCTCA | TACAACACCC | GGCTGGACGC | GCGGCAGGCA | 360 |
| ATGACGAACG | AATTCTACCT | CACCCTGGTA | TATCGGCCTG | CCACACCGC | GCTCGGCAAG | 420 |
| CGTGCGCATC | ACGGCCAGGC | CGAGGTCCGC | CGGCAACTGC | TGGCCCATGT | TCGACGCATG | 480 |
| GACGAAATCG | GATCCCTGAT | CGAAACGACA | CTGCACAGCC | ATGGCGAGAA | CCACGAGCAG | 540 |
| ACCATCACCG | TGCTGGGCTG | CGAGACGGAC | AACACCGGCC | GGCGATACTC | CCGGACGCTG | 600 |
| ACCCTGCTCG | AATTCCTGCT | CACCGGCCAC | TGGCAACCGG | TACGTGTGCC | GACCGGGCCG | 660 |
| GTGGACGCGT | ATCTCGATTC | GAGCCGGATC | CTTGCCGGCG | CCGAAATGAT | GGAGTTGCGT | 720 |
| GCTCCGACCT | GCCGCCGCTA | CGCGCAGTTC | ATCGATTTCA | AGGAATACGG | CACGCACACC | 780 |
| GAACCAGGGA | TGCTGAATGC | CTTGCTGTAC | GAGGATTACG | AATATGTGAT | CACGCATTCG | 840 |
| TTCAGCGCGG | TCGGCAAGCG | ACAGGCGCTG | GCCTACCTGC | AGCGGCAGCG | CGCCCAGCTG | 900 |
| GCCAACGTGC | AGGACGCCGC | GTACTCGCAG | ATCGACGACC | TCGCGCATGC | CGAAGACGCC | 960 |
| CTGGTCAATG | GCGATTTCGT | GATCGGCGAG | TATCACTTCT | CGATGATGAT | CCTCGGCGCC | 1020 |
| GACCCCGGC | AACTGCGGCG | CGATGTCAGT | TCGGCCATGA | CGCGCATCCA | GGAGCGCGGC | 1080 |
| TTTCTCGCCA | CGCCGGTGAC | GTTGGCCCTG | GATGCCGCCT | TCTATGCGCA | ATTGCCTGCC | 1140 |
| AACTGGGCAT | ACCGGTCGCG | CAAGGCCATG | TTGACCAGCA | GAAACTTCGC | CGGACTGTGC | 1200 |
| AGCTTTCATA | ATTTCTACGG | CGGCAAGCGC | GATGGCAACC | CCTGGGGCCC | GGCCCTGAGC | 1260 |
| CTGCTGTCCA | CGCCTTCCGG | GCAACCGTTC | TACTTCAATT | TCCATCACTC | CGGGCTCGAC | 1320 |
| GAGGATTGCC | GCGGCCAGAT | GATGCTGGGC | AACACGCGCA | TCATCGGCCA | GTCCGTCAGC | 1380 |
| GGCAAGACCG | TGCTGCTCAA | TTTCCTGCTT | TGCCAGCTGC | AGAAATTCCG | ATCCGCGGAT | 1440 |
| GCCGATGGCC | TGACGACGAT | TTTCTTCGAC | AAGGACCGGG | CGCGGAAAT | CTGCATCCGC | 1500 |
| GCCCTCGATG | GCCAGTACTT | GCGGATACGC | GACGGCGAAC | CGACCGGCTT | CAACCCCTTG | 1560 |
| CAGCTGCCAT | GCACCGACCG | CAATGTCATG | TTCCTGGACT | CGCTTCTGGC | GATGCTCGCG | 1620 |
| CGCGCTCATG | ACTCGCCGCT | GACGTCGGCG | CAGCACGCGA | CGCTGGCCAC | CGCTGTGCGC | 1680 |
| ACGGTGCTGC | GCATGCCGGC | GTCGCTGCGG | CGAATGTCCA | CGCTGCTGCA | AAACATCACC | 1740 |
| CAGGCCACGT | CCGAGCAGCG | GGAACTGGTC | AGACGCCTGG | GGCGCTGGTG | CCGCGACGAC | 1800 |

| | | | | | | |
|---|---|---|---|---|---|---|
| GGCGCCGGTG | GCACGGGAAT | GCTGTGGTGG | GTCTTCGACA | ATCCGAATGA | TTGCCTCGAT | 1860 |
| TTTTCGCGGC | CGGGCAACTA | CGGCATCGAC | GGCACCGCGT | TCCTGGACAA | TGCCGAGACG | 1920 |
| CGCACGCCGA | TCTCGATGTA | CCTGTTGCAT | CGGATGAACG | AGGCCATGGA | TGGACGGCGC | 1980 |
| TTCGTCTATC | TCATGGACGA | AGCCTGGAAG | TGGATCGACG | ACCCGGCCTT | CGCCGAGTTC | 2040 |
| GCAGGCGACC | AGCAGCTGAC | CATACGCAAG | AAGAACGGGC | TGGGCGTCTT | CTCCACGCAA | 2100 |
| ATGCCAAGCA | GCCTGCTCGG | CGCGAGGGTC | GCCGCATCGC | TGGTACAGCA | ATGCGCAACC | 2160 |
| GAGATCTATC | TGCCCAACCC | CAGGGCCGAT | CGCGCCGAAT | ACCTGGATGG | TTTCAAATGC | 2220 |
| ACCGAAACCG | AGTACCAGTT | GATCCGCTCC | ATGGCGGAGG | ACAGCCATCT | TTTTCTCGTC | 2280 |
| AAACAGGGCA | GGCAGGCAGT | CGTCGCACAA | CTCGACCTCT | CCGGCATGGA | TGACGAATTG | 2340 |
| GCCATCCTGT | CCGGCAACGC | CAGGAACCTG | CGCTGTTTCG | AGCAAGCGCT | GGCACTGACG | 2400 |
| CGGGAGCGCG | ACCCAAACGA | CTGGATCGCG | GTATTCCATC | GGCTTCGACG | CGAAGCCAGC | 2460 |
| GCCGGCCTCA | GGTGAAACCA | GTATGGCCGG | CCTGTCACGA | ATCCTGCTGT | CCTGCACGCT | 2520 |
| TGCATGCCTG | CTCGCCGGGC | AGGCCGCCCA | GGCCTCCGTG | GACGACCCCA | CCCGGGCTGG | 2580 |
| CGGCGACAAT | CGGGTACGGG | CGCTGCGCGC | CGACCAGGCG | CGACGAGACG | TCCTGCTCAC | 2640 |
| CGCCTGCCGC | GACGACCCCG | GCCACCGGCG | CGGTGAGCCG | GATTGCGTCA | ACGCCGAGCG | 2700 |
| CGCCCAGGCG | CTGCAGCAGT | GGCAGGCCGC | CGCCATGACC | AGCGTGGATG | CCGCCTTCTC | 2760 |
| CGATTTGGCT | GGTGCGCTGC | GCAATGCGGC | GCCGCGGCGG | ATGGAGGCCG | CGATCGTACG | 2820 |
| GCTGACGCGC | CAGCTCCAGC | CGCTGGTCTA | TTCCATGATG | ACGCTGCTGG | TACTGTTGAC | 2880 |
| TGGCTATGCA | CTGCTGGCGC | GACGCGACCG | CCCGTTCGAA | TGGCATATCC | GGCACGCCCT | 2940 |
| GCTGGTTGCG | GTCGTGACCT | CGCTGGCACT | GTCTCCCGAC | CGCTACCTGT | CCACCGTGGT | 3000 |
| GGCAGGCGTC | CAGGACGTCG | CGGGCTGGCT | GAGCGGGCCC | TGGACAGCGC | CGGACGGCGC | 3060 |
| GGCGGGGCGC | GGCGGACTCG | CGCAACTGGA | CCAGTTCGCC | GCCCAGGCCC | AGGCCTGGGT | 3120 |
| CGCGCAACTG | GCCGGCCAGG | CCGCCAACGA | CGCCAACCCG | GCAGCGCCG | TCAACTGGCT | 3180 |
| GCTCTGCGCC | ATGATCGTGG | CCGCCAGCGC | GGGAGGCTGG | CTTTGCCTGG | CGGCGTCCCT | 3240 |
| GCTGATCGTG | CCGGGCCTGA | TAGTCACGCT | GCTGCTGTCG | TTGGGGCCGC | TCTTTCTCGT | 3300 |
| GCTGCTGCTG | TTTCCCGCGC | TGCAGCGCTG | GACCAACGCC | TGGCTCGGCG | CGCTGGTCCG | 3360 |
| CGCGCTCGTC | TTCATGGCGC | TGGGCACGCC | GGCCGTCGGC | CTGCTGTCCG | ATGTACTGGC | 3420 |
| TGGCGCCTTG | CCGGCCGGCC | TGCCGCAGCG | GTTTGCCACC | GAGCCGCTGC | GCTCGACCAT | 3480 |
| GCTGGCGGCA | ACGCTATGCG | CCACGGCGAC | ACTCATGCTG | CTGACCCTGG | TCCCGCTGGC | 3540 |
| CAGCAGCGTC | AACGCGGGCC | TGCGGCGCCG | CCTGTGGCCT | AACGCGGCCC | ATCCCGGGCT | 3600 |
| CGCGCAGGCT | CATCGGCAAG | CCGCTGCGCG | CCAGTACGCC | CGCCGTCCGG | CCGCGGCGGC | 3660 |
| CGCCGCCGCG | GGACCGCACC | AGGCCGGTAC | GTACGCAGCC | TCGGCCACGC | CGGCGCCGGC | 3720 |
| GCCGGCCCGC | CCGGCCCCAT | CCTTCCCGGC | GCACGCCTAT | AGGCAGTACG | CCCTGGGCGG | 3780 |
| CGCGAGAAGT | CCCGCCGGCC | CAGGGTGCGA | CGCGACGACC | GGCCCGCGCC | GGCGCCGGAC | 3840 |
| CGACGGGTTC | TTCCCCGCAA | ACCCAACCTG | CCATGATCCA | CGCACATTCC | AACGCCAGAT | 3900 |
| TATTGCGATG | GGCCATCCTG | CCATCGCCC | CCGTCACGCT | CGGCGCCTGC | GCCCGAAGC | 3960 |
| GGGCCGCCCG | GCTTGCCGTA | TCCCGATGGC | AAGCCCCTGA | TTCCCATCAA | CACCGCCGCC | 4020 |
| CCGGAGCAAG | GATCGTCATG | CCAGATCCGC | GCCCCTTGGA | CATCGCCCCC | GTCACGCTCG | 4080 |
| GCGCCTGCGC | CCCGAACGGG | CCGCCCGGCT | TGCCGTATCC | CGATGGCAAG | CCCCTGATTC | 4140 |
| CCATCAACAC | CGCCGCCCCG | GAGCAAGGAT | CGTCATGCCA | GACCCGCGCC | CCTTGACGCC | 4200 |

| | | | | | |
|---|---|---|---|---|---|
| TGACCAGACG | CATGGCCGCG | GGCATGCCGA | GGCCGCGGTG | GACTGGGAAG | CGTCCCGCCT | 4260 |
| GTACCGGCTG | GCGCAGTCGG | AACGCCGTGC | ATGGACGGTG | GCGTGGGCGG | CGCTCGCCGT | 4320 |
| GACCGCGCTG | TCATTGATCG | CCATCGCGAC | GATGCTTCCG | CTCAAGACCA | CCATTCCTTA | 4380 |
| CCTGATCGAG | GTCGAAAAGA | GCAGCGGCGC | GGCCTCGGTC | GTCACGCAAT | TCGAACCCCG | 4440 |
| AGATTTCACC | CCGGACACCT | TGATGAACCA | GTACTGGCTG | ACGCGCTATG | TCACGGCGCG | 4500 |
| CGAGCGCTAC | GATTGGCACA | CGATCCAGCA | CGATTACGAC | TACGTGCGCC | TGCTGTCCGC | 4560 |
| GCCCGCCGTC | AGGCACGATT | ACGAAACCAG | CTACGAGGCG | CCCGATGCGC | CGGACCGCAA | 4620 |
| GTACGGCGCT | GGCACGACCC | TGGCCGTGAA | AATTCTCAGC | GCCATCGACC | ATGGCAAGGG | 4680 |
| CGTCGGCACG | GTGCGCTTTG | TCCGGACACG | GCGCGACGCG | GACGGGCAGG | GCGCCGCCGA | 4740 |
| ATCCTCGATA | TGGGTAGCGA | CCGTGGCATT | CGCCTACGAT | CAGCCGCGCG | CGCTGACCCA | 4800 |
| GGCCCAGCGC | TGGCTCAATC | CGCTGGGCTT | TGCCGTCACC | AGCTATCGCG | TCGACGCGGA | 4860 |
| GGCTGGACAG | CCATGATGGC | GGCACGGATG | ATGGCGGCCG | GCCTGGCGGC | CACGGCGCTT | 4920 |
| TCGGCGCATG | CGTTCCGGAT | ACCCACGCCA | GGAGAACAGG | ACGCCCGCAT | ACAGACCGTG | 4980 |
| CCGTACCACC | CGGAGGAGGT | GGTGCTGGTG | CGCGCCTGGA | ACGGCTACGT | CACCCGGATC | 5040 |
| GTATTCGACG | AGCAGGAGAA | GATCATCGAC | GTCGCCGCGG | GGTTCGCCGA | CGGCTGGCAA | 5100 |
| TTCAGCCCGG | AAGGCAATGT | GCTGTATATC | AAGGCCAAAT | CCTTCCCCGC | GCAGGGCTCG | 5160 |
| CCCGCGCAGG | CGCCGGAGCC | GGGATTGTGG | AACACCAATC | TGCTCGTCAA | AACCGACCGC | 5220 |
| CGGCTCTACG | ACTTCGACCT | GGTGCTGGCC | AGCGCGGACG | CGGCGACACC | GCAGGCGTTG | 5280 |
| CAGCGTTCGC | GCATGGCCTA | TCGCCTGCAA | TTCCGCTACC | GGCCGCGCC | GCAGGCGGCA | 5340 |
| TCCCGCGCCA | GCCCCGTCGG | CCCGGCTGTT | CCCGCCGGCG | CATTGAACCG | GCGCTACGCC | 5400 |
| ATGCAGGTGG | GCAACGGGTC | GGACGGCATC | GCACCCATCG | CTGCGTACGA | CGACGGCCGG | 5460 |
| CATACCTGGC | TCACGTTCAG | ACCGGGTCAG | CCGTTTCCGG | CCGTATTCGC | GGTAGCGCCG | 5520 |
| GACGGAACGG | AAACCCTGGT | CAATCTGCAT | ATCGACAACC | AATCACTGGT | CATACACCGG | 5580 |
| GTAGCGCCGG | TCCTGATGCT | GCGGTCCGGC | GCCAGCGTCA | TCCGGATCGT | CAACCAGAAC | 5640 |
| GGCGATGCGT | CCGAGTCCCC | AGCCTTCGAA | TGCCATGCTG | AACCGGCCCT | CTAGTCCCGA | 5700 |
| TGGCGGCGAA | GCGCACGCTT | GGCCGCCGGA | CCCCGAAATC | CCTGTTTCG | CCAATGCCGA | 5760 |
| GCATGCGCAT | CGGCGTCCGC | TGCGCTGGAT | GTTCGCCCTT | GTCGCCGTGG | CCCTGTCATG | 5820 |
| CCTGCTGGCA | ACGGGGATAT | GGCGCAGCCG | CGCCGCGCCG | CCGCACGCCG | CGACGCAGAC | 5880 |
| CGTCGCGCCG | GCGGGGCAAG | CCCTGCCGCC | GGGGCGCATA | TTCACGGTCC | ACCCACGCGA | 5940 |
| ACCCGAACCG | GCGCCGCTTC | CGGACATGCC | GGCGGCTCCC | GACCCGATCC | TGCCGCAGCC | 6000 |
| GCGGCCGGCG | CCACCCGTAC | CGCCGCCGCC | AATCCGCGCG | CCGTACGACT | ACGATGAACC | 6060 |
| GGCGCCCCGG | CGCGACAGCG | CGGCGCTCAA | GTCCGGCCCG | GCCATGATGG | TCGCCACGGC | 6120 |
| CGCGCGCCTT | GGACAAACCG | AGCGGGCGGG | CATGGCGGAC | GACGGCGTGT | CCGCGGATGC | 6180 |
| GGCCACCCTC | ATCGGCAGGA | ACGTCAGCCG | CGCAACCCGC | TCCGGGGCC | GCGATTACCG | 6240 |
| GCTGCTGCCC | GGCACGTTTA | TCGATTGCAT | CCTGCAGACC | CGGATCGTCA | CCAACGTCCC | 6300 |
| GGGGCTGACG | ACCTGCATCG | TATCGCGGGA | TGTCTACAGC | GCCAGCGGCA | AGCGCGTCCT | 6360 |
| GGTGCCGCGT | GGCACGACAG | TGGTGGGCGA | ATACCGCGCC | GACCTGGCGC | AGGGCTCGCA | 6420 |
| ACGCATCTAC | GTCGCATGGA | GCCGGCTTTT | CATGCCGTCC | GGGCTCACGA | TAGAGCTGGC | 6480 |
| ATCGCCGGCC | GTGGACGGAA | CCGGCGCCGC | GGGGCTGCCC | GGCGTGGTGG | ACGACAAATT | 6540 |
| CGCGCAGCGT | TTCGGCGGCG | CCCTGCTGCT | GAGCGTATTG | GGCGATGCCA | CCTCGTACAT | 6600 |

-continued

```
GCTGGCGCGC GCCACCGATG CGCGCCACGG CGTGAACGTG AACCTTACCG CCGCGGGAAC      6660
GATGAATTCG CTGGCCGCCA GCGCCCTGAA CAACACGATC AACATCCCGC CCACGCTCTA      6720
CAAGAACCAC GGCGACCAGA TCGGCATCCT GGTCGCCCGT CCATTGGACT TCTCCATACT      6780
CAGGGGGACG AATGAATGAT GCCGCGCCGG ATCGACAGGC ATCGGTCGAC TTCCACCTCC      6840
AAGCGCTGCA TCCGTGGCTG AGCCGGCAGG ATATAGCGGA AATCTGCGTG AACCGTCCGG      6900
GGCAGCTCTG GTATGAAGAC CGCAACGGCT GGAACCGCCA GGAGTCGGGC GCGCTCACGC      6960
TTGATCATCT GCACGCCCTG GCTACCGCGA CGGCCCGGTT CTGCGACCGC GACATTTGCC      7020
CGGAGCGTCC CTTGCTGGCG GCGTCCCTGC CTGGCGGCGA ACGGGTGCAG ATCGTCGTCC      7080
CTCCAGCCTG CGAACCGGGC ACGCTGTCGC TGACCATCCG CAAGCCCGCC CGGCGCATCT      7140
GGCCACTATC GGAACTGTTG CGCGATACGC TCGACCTGCC AGGCGTCCCG GGCGCCAGCC      7200
AAGCGCGGCC AGACCCCTTG CTCGACCCGT GGAGGCGCGG CGCATGGGAC GACTTCCTGC      7260
GGCTGGCCGT GCAGGCGGGC AAGGCCATAC TCGTCGCCGG CCAGACCGGT TCGGGCAAGA      7320
CCACATTGAT GAACGCGTTG AGCGGGGAGA TTCCGCCCCG CGAACGCATC GTCACGATCG      7380
AGGACGTGCG CGAGTTGCGG CTGGATCCGG CAACCAATCA CGTACACCTG TTGTTCGGCA      7440
CTCCTACGGA AGGCAGGACG GCCGCCGTAT CGGCCACCGA GCTGTTGCGC GCGGCGCTGC      7500
GCATGGCGCC CACGCGCATC CTGCTGGCGG AGCTGCGCGG GGGAGAAGCC TTCGACTTCC      7560
TCCAGGCATG CGCGTCCGGA CACAGCGGCG GCATCAGCAC CTGCCATGCC GCCAGCGCCG      7620
ATATGGCGCT GCAGCGGCTG ACGCTGATGT GCATGCAACA CCCGAATTGC AGATGCTTC      7680
CCTACTCGAC GCTACGCGCG CTGGTCGAAT CCGTGATCGA TACTCTAGAG GATTCGGCCG      7740
GG                                                                   7742
```

(2) INFORMATION FOR SEQ ID NO:2:

(i) SEQUENCE CHARACTERISTICS:
        (A) LENGTH: 2472 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..2472

(xi) SEQUENCE DESCRIPTION: SEQ ID NO:2:

```
ATG AAC CGG CGC GGC GGC CAG ACC GCA TTT GCG GCC ATT GCG CGC AAC        48
Met Asn Arg Arg Gly Gly Gln Thr Ala Phe Ala Ala Ile Ala Arg Asn
 1               5                  10                  15

GAG CGC GCC ATC GCT GCG TTC ATC CCC TAC AGC AGC CAC CTG ACG GAC        96
Glu Arg Ala Ile Ala Ala Phe Ile Pro Tyr Ser Ser His Leu Thr Asp
             20                  25                  30

ACG ACG CTG ATC ACC CAT GGC GCG GAC CTG GTC CGC ACC TGG CGC GTA       144
Thr Thr Leu Ile Thr His Gly Ala Asp Leu Val Arg Thr Trp Arg Val
         35                  40                  45

CAG GGG ATC GCC TTC GAA AGC GCC GAG CCA GAG CTG GTT TCG CAG CGC       192
Gln Gly Ile Ala Phe Glu Ser Ala Glu Pro Glu Leu Val Ser Gln Arg
     50                  55                  60

CAT GAA CAG CTC AAC GGC CTG TGG CGC GCC ATC TCG TGC GAG CAG GTC       240
His Glu Gln Leu Asn Gly Leu Trp Arg Ala Ile Ser Cys Glu Gln Val
 65                  70                  75                  80

GCG CTT TGG ATC CAT TGC ATC CGG CGC AAG ACG CAG GCC GGG TTG GAT       288
Ala Leu Trp Ile His Cys Ile Arg Arg Lys Thr Gln Ala Gly Leu Asp
                 85                  90                  95
```

-continued

| | | | | | | | | | | | | | | | | |
|---|---|---|---|---|---|---|---|---|---|---|---|---|---|---|---|---|
| GCG | CGG | TAC | GAA | AAT | CCG | TTC | TGC | CGC | GCG | CTC | GAC | GCC | TCA | TAC | AAC | 336 |
| Ala | Arg | Tyr | Glu | Asn | Pro | Phe | Cys | Arg | Ala | Leu | Asp | Ala | Ser | Tyr | Asn | |
| | | | 100 | | | | 105 | | | | | | 110 | | | |
| ACC | CGG | CTG | GAC | GCG | CGG | CAG | GCA | ATG | ACG | AAC | GAA | TTC | TAC | CTC | ACC | 384 |
| Thr | Arg | Leu | Asp | Ala | Arg | Gln | Ala | Met | Thr | Asn | Glu | Phe | Tyr | Leu | Thr | |
| | | 115 | | | | 120 | | | | | 125 | | | | | |
| CTG | GTA | TAT | CGG | CCT | GGC | CAC | ACC | GCG | CTC | GGC | AAG | CGT | GCG | CAT | CAC | 432 |
| Leu | Val | Tyr | Arg | Pro | Gly | His | Thr | Ala | Leu | Gly | Lys | Arg | Ala | His | His | |
| | 130 | | | | 135 | | | | | 140 | | | | | | |
| GGC | CAG | GCC | GAG | GTC | CGC | CGG | CAA | CTG | CTG | GCC | CAT | GTT | CGA | CGC | ATG | 480 |
| Gly | Gln | Ala | Glu | Val | Arg | Arg | Gln | Leu | Leu | Ala | His | Val | Arg | Arg | Met | |
| 145 | | | | 150 | | | | | 155 | | | | | | 160 | |
| GAC | GAA | ATC | GGA | TCC | CTG | ATC | GAA | ACG | ACA | CTG | CAC | AGC | CAT | GGC | GAG | 528 |
| Asp | Glu | Ile | Gly | Ser | Leu | Ile | Glu | Thr | Thr | Leu | His | Ser | His | Gly | Glu | |
| | | | | 165 | | | | 170 | | | | | 175 | | | |
| AAC | CAC | GAG | CAG | ACC | ATC | ACC | GTG | CTG | GGC | TGC | GAG | ACG | GAC | AAC | ACC | 576 |
| Asn | His | Glu | Gln | Thr | Ile | Thr | Val | Leu | Gly | Cys | Glu | Thr | Asp | Asn | Thr | |
| | | | 180 | | | | 185 | | | | | 190 | | | | |
| GGC | CGG | CGA | TAC | TCC | CGG | ACG | CTG | ACC | CTG | CTC | GAA | TTC | CTG | CTC | ACC | 624 |
| Gly | Arg | Arg | Tyr | Ser | Arg | Thr | Leu | Thr | Leu | Leu | Glu | Phe | Leu | Leu | Thr | |
| | 195 | | | | | 200 | | | | | 205 | | | | | |
| GGC | CAC | TGG | CAA | CCG | GTA | CGT | GTG | CCG | ACC | GGG | CCG | GTG | GAC | GCG | TAT | 672 |
| Gly | His | Trp | Gln | Pro | Val | Arg | Val | Pro | Thr | Gly | Pro | Val | Asp | Ala | Tyr | |
| | 210 | | | | | 215 | | | | | 220 | | | | | |
| CTC | GAT | TCG | AGC | CGG | ATC | CTT | GCC | GGC | GCC | GAA | ATG | ATG | GAG | TTG | CGT | 720 |
| Leu | Asp | Ser | Ser | Arg | Ile | Leu | Ala | Gly | Ala | Glu | Met | Met | Glu | Leu | Arg | |
| 225 | | | | | 230 | | | | | 235 | | | | | 240 | |
| GCT | CCG | ACC | TGC | CGC | CGC | TAC | GCG | CAG | TTC | ATC | GAT | TTC | AAG | GAA | TAC | 768 |
| Ala | Pro | Thr | Cys | Arg | Arg | Tyr | Ala | Gln | Phe | Ile | Asp | Phe | Lys | Glu | Tyr | |
| | | | | 245 | | | | | 250 | | | | | 255 | | |
| GGC | ACG | CAC | ACC | GAA | CCA | GGG | ATG | CTG | AAT | GCC | TTG | CTG | TAC | GAG | GAT | 816 |
| Gly | Thr | His | Thr | Glu | Pro | Gly | Met | Leu | Asn | Ala | Leu | Leu | Tyr | Glu | Asp | |
| | | | 260 | | | | | 265 | | | | | 270 | | | |
| TAC | GAA | TAT | GTG | ATC | ACG | CAT | TCG | TTC | AGC | GCG | GTC | GGC | AAG | CGA | CAG | 864 |
| Tyr | Glu | Tyr | Val | Ile | Thr | His | Ser | Phe | Ser | Ala | Val | Gly | Lys | Arg | Gln | |
| | | 275 | | | | | 280 | | | | | 285 | | | | |
| GCG | CTG | GCC | TAC | CTG | CAG | CGG | CAG | CGC | GCC | CAG | CTG | GCC | AAC | GTG | CAG | 912 |
| Ala | Leu | Ala | Tyr | Leu | Gln | Arg | Gln | Arg | Ala | Gln | Leu | Ala | Asn | Val | Gln | |
| | 290 | | | | | 295 | | | | | 300 | | | | | |
| GAC | GCC | GCG | TAC | TCG | CAG | ATC | GAC | GAC | CTC | GCG | CAT | GCC | GAA | GAC | GCC | 960 |
| Asp | Ala | Ala | Tyr | Ser | Gln | Ile | Asp | Asp | Leu | Ala | His | Ala | Glu | Asp | Ala | |
| 305 | | | | 310 | | | | | 315 | | | | | 320 | | |
| CTG | GTC | AAT | GGC | GAT | TTC | GTG | ATC | GGC | GAG | TAT | CAC | TTC | TCG | ATG | ATG | 1008 |
| Leu | Val | Asn | Gly | Asp | Phe | Val | Ile | Gly | Glu | Tyr | His | Phe | Ser | Met | Met | |
| | | | | 325 | | | | | 330 | | | | | 335 | | |
| ATC | CTC | GGC | GCC | GAC | CCC | CGG | CAA | CTG | CGG | CGC | GAT | GTC | AGT | TCG | GCC | 1056 |
| Ile | Leu | Gly | Ala | Asp | Pro | Arg | Gln | Leu | Arg | Arg | Asp | Val | Ser | Ser | Ala | |
| | | | 340 | | | | | 345 | | | | | 350 | | | |
| ATG | ACG | CGC | ATC | CAG | GAG | CGC | GGC | TTT | CTC | GCC | ACG | CCG | GTG | ACG | TTG | 1104 |
| Met | Thr | Arg | Ile | Gln | Glu | Arg | Gly | Phe | Leu | Ala | Thr | Pro | Val | Thr | Leu | |
| | | 355 | | | | | 360 | | | | | 365 | | | | |
| GCC | CTG | GAT | GCC | GCC | TTT | TAT | GCG | CAA | TTG | CCT | GCC | AAC | TGG | GCA | TAC | 1152 |
| Ala | Leu | Asp | Ala | Ala | Phe | Tyr | Ala | Gln | Leu | Pro | Ala | Asn | Trp | Ala | Tyr | |
| | 370 | | | | | 375 | | | | | 380 | | | | | |
| CGG | TCG | CGC | AAG | GCC | ATG | TTG | ACC | AGC | AGA | AAC | TTC | GCC | GGA | CTG | TGC | 1200 |
| Arg | Ser | Arg | Lys | Ala | Met | Leu | Thr | Ser | Arg | Asn | Phe | Ala | Gly | Leu | Cys | |
| 385 | | | | | 390 | | | | | 395 | | | | | 400 | |
| AGC | TTT | CAT | AAT | TTC | TAC | GGC | GGC | AAG | CGC | GAT | GGC | AAC | CCC | TGG | GGC | 1248 |
| Ser | Phe | His | Asn | Phe | Tyr | Gly | Gly | Lys | Arg | Asp | Gly | Asn | Pro | Trp | Gly | |
| | | | | 405 | | | | | 410 | | | | | 415 | | |

```
CCG GCC CTG AGC CTG CTG TCC ACG CCT TCC GGG CAA CCG TTC TAC TTC    1296
Pro Ala Leu Ser Leu Leu Ser Thr Pro Ser Gly Gln Pro Phe Tyr Phe
            420                 425                 430

AAT TTC CAT CAC TCC GGG CTC GAC GAG GAT TGC CGC GGC CAG ATG ATG    1344
Asn Phe His His Ser Gly Leu Asp Glu Asp Cys Arg Gly Gln Met Met
            435                 440                 445

CTG GGC AAC ACG CGC ATC ATC GGC CAG TCC GTC AGC GGC AAG ACC GTG    1392
Leu Gly Asn Thr Arg Ile Ile Gly Gln Ser Val Ser Gly Lys Thr Val
450                     455                 460

CTG CTC AAT TTC CTG CTT TGC CAG CTG CAG AAA TTC CGA TCC GCG GAT    1440
Leu Leu Asn Phe Leu Leu Cys Gln Leu Gln Lys Phe Arg Ser Ala Asp
465                     470                 475                 480

GCC GAT GGC CTG ACG ACG ATT TTC TTC GAC AAG GAC CGG GGC GCG GAA    1488
Ala Asp Gly Leu Thr Thr Ile Phe Phe Asp Lys Asp Arg Gly Ala Glu
                    485                 490                 495

ATC TGC ATC CGC GCC CTC GAT GGC CAG TAC TTG CGG ATA CGC GAC GGC    1536
Ile Cys Ile Arg Ala Leu Asp Gly Gln Tyr Leu Arg Ile Arg Asp Gly
                500                 505                 510

GAA CCG ACC GGC TTC AAC CCC TTG CAG CTG CCA TGC ACC GAC CGC AAT    1584
Glu Pro Thr Gly Phe Asn Pro Leu Gln Leu Pro Cys Thr Asp Arg Asn
            515                 520                 525

GTC ATG TTC CTG GAC TCG CTT CTG GCG ATG CTC GCG CGC GCT CAT GAC    1632
Val Met Phe Leu Asp Ser Leu Leu Ala Met Leu Ala Arg Ala His Asp
        530                 535                 540

TCG CCG CTG ACG TCG GCG CAG CAC GCG ACG CTG GCC ACC GCT GTG CGC    1680
Ser Pro Leu Thr Ser Ala Gln His Ala Thr Leu Ala Thr Ala Val Arg
545                 550                 555                 560

ACG GTG CTG CGC ATG CCG GCG TCG CTG CGG CGA ATG TCC ACG CTG CTG    1728
Thr Val Leu Arg Met Pro Ala Ser Leu Arg Arg Met Ser Thr Leu Leu
                565                 570                 575

CAA AAC ATC ACC CAG GCC ACG TCC GAG CAG CGG GAA CTG GTC AGA CGC    1776
Gln Asn Ile Thr Gln Ala Thr Ser Glu Gln Arg Glu Leu Val Arg Arg
            580                 585                 590

CTG GGG CGC TGG TGC CGC GAC GAC GGC GCC GGT GGC ACG GGA ATG CTG    1824
Leu Gly Arg Trp Cys Arg Asp Asp Gly Ala Gly Gly Thr Gly Met Leu
        595                 600                 605

TGG TGG GTC TTC GAC AAT CCG AAT GAT TGC CTC GAT TTT TCG CGG CCG    1872
Trp Trp Val Phe Asp Asn Pro Asn Asp Cys Leu Asp Phe Ser Arg Pro
610                 615                 620

GGC AAC TAC GGC ATC GAC GGC ACC GCG TTC CTG GAC AAT GCC GAG ACG    1920
Gly Asn Tyr Gly Ile Asp Gly Thr Ala Phe Leu Asp Asn Ala Glu Thr
625                 630                 635                 640

CGC ACG CCG ATC TCG ATG TAC CTG TTG CAT CGG ATG AAC GAG GCC ATG    1968
Arg Thr Pro Ile Ser Met Tyr Leu Leu His Arg Met Asn Glu Ala Met
                645                 650                 655

GAT GGA CGG CGC TTC GTC TAT CTC ATG GAC GAA GCC TGG AAG TGG ATC    2016
Asp Gly Arg Arg Phe Val Tyr Leu Met Asp Glu Ala Trp Lys Trp Ile
            660                 665                 670

GAC GAC CCG GCC TTC GCC GAG TTC GCA GGC GAC CAG CAG CTG ACC ATA    2064
Asp Asp Pro Ala Phe Ala Glu Phe Ala Gly Asp Gln Gln Leu Thr Ile
        675                 680                 685

CGC AAG AAG AAC GGG CTG GGC GTC TTC TCC ACG CAA ATG CCA AGC AGC    2112
Arg Lys Lys Asn Gly Leu Gly Val Phe Ser Thr Gln Met Pro Ser Ser
690                 695                 700

CTG CTC GGC GCG AGG GTC GCC GCA TCG CTG GTA CAG CAA TGC GCA ACC    2160
Leu Leu Gly Ala Arg Val Ala Ala Ser Leu Val Gln Gln Cys Ala Thr
705                 710                 715                 720

GAG ATC TAT CTG CCC AAC CCC AGG GCC GAT CGC GCC GAA TAC CTG GAT    2208
Glu Ile Tyr Leu Pro Asn Pro Arg Ala Asp Arg Ala Glu Tyr Leu Asp
                725                 730                 735
```

```
GGT TTC AAA TGC ACC GAA ACC GAG TAC CAG TTG ATC CGC TCC ATG GCG    2256
Gly Phe Lys Cys Thr Glu Thr Glu Tyr Gln Leu Ile Arg Ser Met Ala
            740                 745                 750

GAG GAC AGC CAT CTT TTT CTC GTC AAA CAG GGC AGG CAG GCA GTC GTC    2304
Glu Asp Ser His Leu Phe Leu Val Lys Gln Gly Arg Gln Ala Val Val
        755                 760                 765

GCA CAA CTC GAC CTC TCC GGC ATG GAT GAC GAA TTG GCC ATC CTG TCC    2352
Ala Gln Leu Asp Leu Ser Gly Met Asp Asp Glu Leu Ala Ile Leu Ser
        770                 775                 780

GGC AAC GCC AGG AAC CTG CGC TGT TTC GAG CAA GCG CTG GCA CTG ACG    2400
Gly Asn Ala Arg Asn Leu Arg Cys Phe Glu Gln Ala Leu Ala Leu Thr
785                 790                 795                 800

CGG GAG CGC GAC CCA AAC GAC TGG ATC GCG GTA TTC CAT CGG CTT CGA    2448
Arg Glu Arg Asp Pro Asn Asp Trp Ile Ala Val Phe His Arg Leu Arg
                805                 810                 815

CGC GAA GCC AGC GCC GGC CTC AGG                                    2472
Arg Glu Ala Ser Ala Gly Leu Arg
            820
```

( 2 ) INFORMATION FOR SEQ ID NO:3:

( i ) SEQUENCE CHARACTERISTICS:
      ( A ) LENGTH: 824 amino acids
      ( B ) TYPE: amino acid
      ( D ) TOPOLOGY: linear ( i i ) MOLECULE TYPE: protein ( x i ) SEQUENCE DESCRIPTION: SEQ ID NO:3:

```
Met Asn Arg Arg Gly Gly Gln Thr Ala Phe Ala Ala Ile Ala Arg Asn
 1               5                  10                  15

Glu Arg Ala Ile Ala Ala Phe Ile Pro Tyr Ser Ser His Leu Thr Asp
                20                  25                  30

Thr Thr Leu Ile Thr His Gly Ala Asp Leu Val Arg Thr Trp Arg Val
            35                  40                  45

Gln Gly Ile Ala Phe Glu Ser Ala Glu Pro Glu Leu Val Ser Gln Arg
        50                  55                  60

His Glu Gln Leu Asn Gly Leu Trp Arg Ala Ile Ser Cys Glu Gln Val
65                  70                  75                  80

Ala Leu Trp Ile His Cys Ile Arg Arg Lys Thr Gln Ala Gly Leu Asp
                85                  90                  95

Ala Arg Tyr Glu Asn Pro Phe Cys Arg Ala Leu Asp Ala Ser Tyr Asn
            100                 105                 110

Thr Arg Leu Asp Ala Arg Gln Ala Met Thr Asn Glu Phe Tyr Leu Thr
        115                 120                 125

Leu Val Tyr Arg Pro Gly His Thr Ala Leu Gly Lys Arg Ala His His
    130                 135                 140

Gly Gln Ala Glu Val Arg Arg Gln Leu Leu Ala His Val Arg Arg Met
145                 150                 155                 160

Asp Glu Ile Gly Ser Leu Ile Glu Thr Thr Leu His Ser His Gly Glu
                165                 170                 175

Asn His Glu Gln Thr Ile Thr Val Leu Gly Cys Glu Thr Asp Asn Thr
            180                 185                 190

Gly Arg Arg Tyr Ser Arg Thr Leu Thr Leu Glu Phe Leu Leu Thr
        195                 200                 205

Gly His Trp Gln Pro Val Arg Val Pro Thr Gly Pro Val Asp Ala Tyr
    210                 215                 220

Leu Asp Ser Ser Arg Ile Leu Ala Gly Ala Glu Met Met Glu Leu Arg
```

-continued

```
225                     230                     235                     240
Ala Pro Thr Cys Arg Arg Tyr Ala Gln Phe Ile Asp Phe Lys Glu Tyr
                245                     250                     255
Gly Thr His Thr Glu Pro Gly Met Leu Asn Ala Leu Leu Tyr Glu Asp
                260                     265                     270
Tyr Glu Tyr Val Ile Thr His Ser Phe Ser Ala Val Gly Lys Arg Gln
                275                     280                     285
Ala Leu Ala Tyr Leu Gln Arg Gln Arg Ala Gln Leu Ala Asn Val Gln
                290                     295                     300
Asp Ala Ala Tyr Ser Gln Ile Asp Asp Leu Ala His Ala Glu Asp Ala
305                     310                     315                     320
Leu Val Asn Gly Asp Phe Val Ile Gly Glu Tyr His Phe Ser Met Met
                325                     330                     335
Ile Leu Gly Ala Asp Pro Arg Gln Leu Arg Arg Asp Val Ser Ser Ala
                340                     345                     350
Met Thr Arg Ile Gln Glu Arg Gly Phe Leu Ala Thr Pro Val Thr Leu
                355                     360                     365
Ala Leu Asp Ala Ala Phe Tyr Ala Gln Leu Pro Ala Asn Trp Ala Tyr
                370                     375                     380
Arg Ser Arg Lys Ala Met Leu Thr Ser Arg Asn Phe Ala Gly Leu Cys
385                     390                     395                     400
Ser Phe His Asn Phe Tyr Gly Gly Lys Arg Asp Gly Asn Pro Trp Gly
                        405                     410                     415
Pro Ala Leu Ser Leu Leu Ser Thr Pro Ser Gly Gln Pro Phe Tyr Phe
                420                     425                     430
Asn Phe His His Ser Gly Leu Asp Glu Asp Cys Arg Gly Gln Met Met
                435                     440                     445
Leu Gly Asn Thr Arg Ile Ile Gly Gln Ser Val Ser Gly Lys Thr Val
        450                     455                     460
Leu Leu Asn Phe Leu Leu Cys Gln Leu Gln Lys Phe Arg Ser Ala Asp
465                     470                     475                     480
Ala Asp Gly Leu Thr Thr Ile Phe Phe Asp Lys Asp Arg Gly Ala Glu
                        485                     490                     495
Ile Cys Ile Arg Ala Leu Asp Gly Gln Tyr Leu Arg Ile Arg Asp Gly
                500                     505                     510
Glu Pro Thr Gly Phe Asn Pro Leu Gln Leu Pro Cys Thr Asp Arg Asn
        515                     520                     525
Val Met Phe Leu Asp Ser Leu Leu Ala Met Leu Ala Arg Ala His Asp
        530                     535                     540
Ser Pro Leu Thr Ser Ala Gln His Ala Thr Leu Ala Thr Ala Val Arg
545                     550                     555                     560
Thr Val Leu Arg Met Pro Ala Ser Leu Arg Arg Met Ser Thr Leu Leu
                        565                     570                     575
Gln Asn Ile Thr Gln Ala Thr Ser Glu Gln Arg Glu Leu Val Arg Arg
                580                     585                     590
Leu Gly Arg Trp Cys Arg Asp Asp Gly Ala Gly Gly Thr Gly Met Leu
                595                     600                     605
Trp Trp Val Phe Asp Asn Pro Asn Asp Cys Leu Asp Phe Ser Arg Pro
        610                     615                     620
Gly Asn Tyr Gly Ile Asp Gly Thr Ala Phe Leu Asp Asn Ala Glu Thr
625                     630                     635                     640
Arg Thr Pro Ile Ser Met Tyr Leu Leu His Arg Met Asn Glu Ala Met
                        645                     650                     655
```

| | | | | | | | | | | | | | | | | |
|---|---|---|---|---|---|---|---|---|---|---|---|---|---|---|---|---|
| Asp | Gly | Arg | Arg<br>660 | Phe | Val | Tyr | Leu | Met<br>665 | Asp | Glu | Ala | Trp | Lys<br>670 | Trp | Ile | |
| Asp | Asp | Pro<br>675 | Ala | Phe | Ala | Glu | Phe<br>680 | Ala | Gly | Asp | Gln | Gln<br>685 | Leu | Thr | Ile | |
| Arg | Lys<br>690 | Lys | Asn | Gly | Leu | Gly<br>695 | Val | Phe | Ser | Thr | Gln<br>700 | Met | Pro | Ser | Ser | |
| Leu<br>705 | Leu | Gly | Ala | Arg | Val<br>710 | Ala | Ala | Ser | Leu | Val<br>715 | Gln | Gln | Cys | Ala | Thr<br>720 | |
| Glu | Ile | Tyr | Leu | Pro<br>725 | Asn | Pro | Arg | Ala<br>730 | Asp | Arg | Ala | Glu | Tyr<br>735 | Leu | Asp | |
| Gly | Phe | Lys | Cys<br>740 | Thr | Glu | Thr | Glu | Tyr<br>745 | Gln | Leu | Ile | Arg | Ser<br>750 | Met | Ala | |
| Glu | Asp | Ser<br>755 | His | Leu | Phe | Leu | Val<br>760 | Lys | Gln | Gly | Arg | Gln<br>765 | Ala | Val | Val | |
| Ala | Gln<br>770 | Leu | Asp | Leu | Ser | Gly<br>775 | Met | Asp | Asp | Glu | Leu<br>780 | Ala | Ile | Leu | Ser | |
| Gly<br>785 | Asn | Ala | Arg | Asn | Leu<br>790 | Arg | Cys | Phe | Glu | Gln<br>795 | Ala | Leu | Ala | Leu | Thr<br>800 | |
| Arg | Glu | Arg | Asp | Pro<br>805 | Asn | Asp | Trp | Ile | Ala<br>810 | Val | Phe | His | Arg | Leu<br>815 | Arg | |
| Arg | Glu | Ala | Ser<br>820 | Ala | Gly | Leu | Arg | | | | | | | | | |

( 2 ) INFORMATION FOR SEQ ID NO:4:

( i ) SEQUENCE CHARACTERISTICS:
        ( A ) LENGTH: 1515 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1515

( x i ) SEQUENCE DESCRIPTION: SEQ ID NO:4:

| | | | | | | | | | | | | | | | | |
|---|---|---|---|---|---|---|---|---|---|---|---|---|---|---|---|---|
| ATG | GCC | GGC | CTG | TCA | CGA | ATC | CTG | CTG | TCC | TGC | ACG | CTT | GCA | TGC | CTG | 48 |
| Met<br>1 | Ala | Gly | Leu | Ser<br>5 | Arg | Ile | Leu | Leu | Ser<br>10 | Cys | Thr | Leu | Ala | Cys<br>15 | Leu | |
| CTC | GCC | GGG | CAG | GCC | GCC | CAG | GCC | TCC | GTG | GAC | GAC | CCC | ACC | CGG | GCT | 96 |
| Leu | Ala | Gly | Gln<br>20 | Ala | Ala | Gln | Ala | Ser<br>25 | Val | Asp | Asp | Pro | Thr<br>30 | Arg | Ala | |
| GGC | GGC | GAC | AAT | CGG | GTA | CGG | GCG | CTG | CGC | GCC | GAC | CAG | GCG | CGA | CGA | 144 |
| Gly | Gly | Asp<br>35 | Asn | Arg | Val | Arg | Ala<br>40 | Leu | Arg | Ala | Asp | Gln<br>45 | Ala | Arg | Arg | |
| GAC | GTC | CTG | CTC | ACC | GCC | TGC | CGC | GAC | GAC | CCC | GGC | CAC | CGG | CGC | GGT | 192 |
| Asp | Val | Leu<br>50 | Leu | Thr | Ala | Cys<br>55 | Arg | Asp | Asp | Pro | Gly<br>60 | His | Arg | Arg | Gly | |
| GAG | CCG | GAT | TGC | GTC | AAC | GCC | GAG | CGC | GCC | CAG | GCG | CTG | CAG | CAG | TGG | 240 |
| Glu | Pro | Asp | Cys<br>65 | Val | Asn | Ala<br>70 | Glu | Arg | Ala | Gln<br>75 | Ala | Leu | Gln | Gln | Trp<br>80 | |
| CAG | GCC | GCC | GCC | ATG | ACC | AGC | GTG | GAT | GCC | GCC | TTC | TCC | GAT | TTG | GCT | 288 |
| Gln | Ala | Ala | Ala | Met<br>85 | Thr | Ser | Val | Asp | Ala<br>90 | Ala | Phe | Ser | Asp | Leu<br>95 | Ala | |
| GGT | GCG | CTG | CGC | AAT | GCG | GCG | CCG | CGG | CGG | ATG | GAG | GCC | GCG | ATC | GTA | 336 |
| Gly | Ala | Leu | Arg<br>100 | Asn | Ala | Ala | Pro | Arg<br>105 | Arg | Met | Glu | Ala | Ala<br>110 | Ile | Val | |
| CGG | CTG | ACG | CGC | CAG | CTC | CAG | CCG | CTG | GTC | TAT | TCC | ATG | ATG | ACG | CTG | 384 |
| Arg | Leu | Thr | Arg | Gln<br>115 | Leu | Gln | Pro | Leu | Val<br>120 | Tyr | Ser | Met | Met | Thr<br>125 | Leu | |

-continued

|  | 115 | | | | | 120 | | | | | 125 | | | | |  |
|---|---|---|---|---|---|---|---|---|---|---|---|---|---|---|---|---|
| CTG | GTA | CTG | TTG | ACT | GGC | TAT | GCA | CTG | CTG | GCG | CGA | CGC | GAC | CGC | CCG | 432 |
| Leu | Val | Leu | Leu | Thr | Gly | Tyr | Ala | Leu | Leu | Ala | Arg | Arg | Asp | Arg | Pro | |
| | 130 | | | | | 135 | | | | | 140 | | | | | |
| TTC | GAA | TGG | CAT | ATC | CGG | CAC | GCC | CTG | CTG | GTT | GCG | GTC | GTG | ACC | TCG | 480 |
| Phe | Glu | Trp | His | Ile | Arg | His | Ala | Leu | Leu | Val | Ala | Val | Val | Thr | Ser | |
| 145 | | | | | 150 | | | | | 155 | | | | | 160 | |
| CTG | GCA | CTG | TCT | CCC | GAC | CGC | TAC | CTG | TCC | ACC | GTG | GTG | GCA | GGC | GTC | 528 |
| Leu | Ala | Leu | Ser | Pro | Asp | Arg | Tyr | Leu | Ser | Thr | Val | Val | Ala | Gly | Val | |
| | | | | 165 | | | | | 170 | | | | | 175 | | |
| CAG | GAC | GTC | GCG | GGC | TGG | CTG | AGC | GGG | CCC | TGG | ACA | GCG | CCG | GAC | GGC | 576 |
| Gln | Asp | Val | Ala | Gly | Trp | Leu | Ser | Gly | Pro | Trp | Thr | Ala | Pro | Asp | Gly | |
| | | | 180 | | | | | 185 | | | | | 190 | | | |
| GCG | GCG | GGG | CGC | GGC | GGA | CTC | GCG | CAA | CTG | GAC | CAG | TTC | GCC | GCC | CAG | 624 |
| Ala | Ala | Gly | Arg | Gly | Gly | Leu | Ala | Gln | Leu | Asp | Gln | Phe | Ala | Ala | Gln | |
| | | 195 | | | | | 200 | | | | | 205 | | | | |
| GCC | CAG | GCC | TGG | GTC | GCG | CAA | CTG | GCC | GGC | CAG | GCC | GCC | AAC | GAC | GCC | 672 |
| Ala | Gln | Ala | Trp | Val | Ala | Gln | Leu | Ala | Gly | Gln | Ala | Ala | Asn | Asp | Ala | |
| | 210 | | | | | 215 | | | | | 220 | | | | | |
| AAC | CCG | GGC | AGC | GCC | GTC | AAC | TGG | CTG | CTC | TGC | GCC | ATG | ATC | GTG | GCC | 720 |
| Asn | Pro | Gly | Ser | Ala | Val | Asn | Trp | Leu | Leu | Cys | Ala | Met | Ile | Val | Ala | |
| 225 | | | | | 230 | | | | | 235 | | | | | 240 | |
| GCC | AGC | GCG | GGA | GGC | TGG | CTT | TGC | CTG | GCG | GCG | TCC | CTG | CTG | ATC | GTG | 768 |
| Ala | Ser | Ala | Gly | Gly | Trp | Leu | Cys | Leu | Ala | Ala | Ser | Leu | Leu | Ile | Val | |
| | | | | 245 | | | | | 250 | | | | | 255 | | |
| CCG | GGC | CTG | ATA | GTC | ACG | CTG | CTG | CTG | TCG | TTG | GGG | CCG | CTC | TTT | CTC | 816 |
| Pro | Gly | Leu | Ile | Val | Thr | Leu | Leu | Leu | Ser | Leu | Gly | Pro | Leu | Phe | Leu | |
| | | | 260 | | | | | 265 | | | | | 270 | | | |
| GTG | CTG | CTG | CTG | TTT | CCC | GCG | CTG | CAG | CGC | TGG | ACC | AAC | GCC | TGG | CTC | 864 |
| Val | Leu | Leu | Leu | Phe | Pro | Ala | Leu | Gln | Arg | Trp | Thr | Asn | Ala | Trp | Leu | |
| | | 275 | | | | | 280 | | | | | 285 | | | | |
| GGC | GCG | CTG | GTC | CGC | GCG | CTC | GTC | TTC | ATG | GCG | CTG | GGC | ACG | CCG | GCC | 912 |
| Gly | Ala | Leu | Val | Arg | Ala | Leu | Val | Phe | Met | Ala | Leu | Gly | Thr | Pro | Ala | |
| | 290 | | | | | 295 | | | | | 300 | | | | | |
| GTC | GGC | CTG | CTG | TCC | GAT | GTA | CTG | GCT | GGC | GCC | TTG | CCG | GCC | GGC | CTG | 960 |
| Val | Gly | Leu | Leu | Ser | Asp | Val | Leu | Ala | Gly | Ala | Leu | Pro | Ala | Gly | Leu | |
| 305 | | | | | 310 | | | | | 315 | | | | | 320 | |
| CCG | CAG | CGG | TTT | GCC | ACC | GAG | CCG | CTG | CGC | TCG | ACC | ATG | CTG | GCG | GCA | 1008 |
| Pro | Gln | Arg | Phe | Ala | Thr | Glu | Pro | Leu | Arg | Ser | Thr | Met | Leu | Ala | Ala | |
| | | | | 325 | | | | | 330 | | | | | 335 | | |
| ACG | CTA | TGC | GCC | ACG | GCG | ACA | CTC | ATG | CTG | CTG | ACC | CTG | GTC | CCG | CTG | 1056 |
| Thr | Leu | Cys | Ala | Thr | Ala | Thr | Leu | Met | Leu | Leu | Thr | Leu | Val | Pro | Leu | |
| | | | 340 | | | | | 345 | | | | | 350 | | | |
| GCC | AGC | AGC | GTC | AAC | GCG | GGC | CTG | CGG | CGC | CGC | CTG | TGG | CCT | AAC | GCG | 1104 |
| Ala | Ser | Ser | Val | Asn | Ala | Gly | Leu | Arg | Arg | Arg | Leu | Trp | Pro | Asn | Ala | |
| | | 355 | | | | | 360 | | | | | 365 | | | | |
| GCC | CAT | CCC | GGG | CTC | GCG | CAG | GCT | CAT | CGG | CAA | GCC | GCT | GCG | CGC | CAG | 1152 |
| Ala | His | Pro | Gly | Leu | Ala | Gln | Ala | His | Arg | Gln | Ala | Ala | Ala | Arg | Gln | |
| | 370 | | | | | 375 | | | | | 380 | | | | | |
| TAC | GCC | CGC | CGT | CCG | GCC | GCG | GCG | GCC | GCC | GCG | GGA | CCG | CAC | CAG | | 1200 |
| Tyr | Ala | Arg | Arg | Pro | Ala | Ala | Ala | Ala | Ala | Ala | Gly | Pro | His | Gln | | |
| 385 | | | | | 390 | | | | | 395 | | | | | 400 | |
| GCC | GGT | ACG | TAC | GCA | GCC | TCG | GCC | ACG | CCG | GCG | CCG | GCC | CGC | | | 1248 |
| Ala | Gly | Thr | Tyr | Ala | Ala | Ser | Ala | Thr | Pro | Ala | Pro | Ala | Arg | | | |
| | | | | 405 | | | | | 410 | | | | | 415 | | |
| CCG | GCC | CCA | TCC | TTC | CCG | GCG | CAC | GCC | TAT | AGG | CAG | TAC | GCC | CTG | GGC | 1296 |
| Pro | Ala | Pro | Ser | Phe | Pro | Ala | His | Ala | Tyr | Arg | Gln | Tyr | Ala | Leu | Gly | |
| | | | 420 | | | | | 425 | | | | | 430 | | | |
| GGC | GCG | AGA | AGT | CCC | GCC | GGC | CCA | GGG | TGC | GAC | GCG | ACG | ACC | GGC | CCG | 1344 |
| Gly | Ala | Arg | Ser | Pro | Ala | Gly | Pro | Gly | Cys | Asp | Ala | Thr | Thr | Gly | Pro | |

|  |  |  |  |  |  |  |  |  |  |  |  |  |  |  |  |
|---|---|---|---|---|---|---|---|---|---|---|---|---|---|---|---|
| | | 435 | | | | | 440 | | | | | | 445 | | |
| CGC | CGG | CGC | CGG | ACC | GAC | GGG | TTC | TTC | CCC | GCA | AAC | CCA | ACC | TGC | CAT | 1392
| Arg | Arg | Arg | Arg | Thr | Asp | Gly | Phe | Phe | Pro | Ala | Asn | Pro | Thr | Cys | His |
| 450 | | | | | 455 | | | | | 460 | | | | | |
| GAT | CCA | CGC | ACA | TTC | CAA | CGC | CAG | ATT | ATT | GCG | ATG | GGC | CAT | CCT | GGC | 1440
| Asp | Pro | Arg | Thr | Phe | Gln | Arg | Gln | Ile | Ile | Ala | Met | Gly | His | Pro | Gly |
| 465 | | | | 470 | | | | | 475 | | | | | | 480 |
| CAT | CGC | CCC | CGT | CAC | GCT | CGG | CGC | CTG | CGC | CCC | GAA | GCG | GGC | CGC | CCG | 1488
| His | Arg | Pro | Arg | His | Ala | Arg | Arg | Leu | Arg | Pro | Glu | Ala | Gly | Arg | Pro |
| | | | | 485 | | | | | 490 | | | | | 495 | |
| GCT | TGC | CGT | ATC | CCG | ATG | GCA | AGC | CCC | | | | | | | | 1515
| Ala | Cys | Arg | Ile | Pro | Met | Ala | Ser | Pro | | | | | | | |
| | | | 500 | | | | | 505 | | | | | | | |

( 2 ) INFORMATION FOR SEQ ID NO:5:

( i ) SEQUENCE CHARACTERISTICS:
        ( A ) LENGTH: 505 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Met | Ala | Gly | Leu | Ser | Arg | Ile | Leu | Leu | Ser | Cys | Thr | Leu | Ala | Cys | Leu |
|---|---|---|---|---|---|---|---|---|---|---|---|---|---|---|---|
| 1 | | | | 5 | | | | | 10 | | | | | 15 | |
| Leu | Ala | Gly | Gln | Ala | Ala | Gln | Ala | Ser | Val | Asp | Asp | Pro | Thr | Arg | Ala |
| | | | 20 | | | | | 25 | | | | | 30 | | |
| Gly | Gly | Asp | Asn | Arg | Val | Arg | Ala | Leu | Arg | Ala | Asp | Gln | Ala | Arg | Arg |
| | | | 35 | | | | | 40 | | | | | 45 | | |
| Asp | Val | Leu | Leu | Thr | Ala | Cys | Arg | Asp | Asp | Pro | Gly | His | Arg | Arg | Gly |
| | 50 | | | | | 55 | | | | | 60 | | | | |
| Glu | Pro | Asp | Cys | Val | Asn | Ala | Glu | Arg | Ala | Gln | Ala | Leu | Gln | Gln | Trp |
| 65 | | | | | 70 | | | | | 75 | | | | | 80 |
| Gln | Ala | Ala | Ala | Met | Thr | Ser | Val | Asp | Ala | Ala | Phe | Ser | Asp | Leu | Ala |
| | | | | 85 | | | | | 90 | | | | | 95 | |
| Gly | Ala | Leu | Arg | Asn | Ala | Ala | Pro | Arg | Arg | Met | Glu | Ala | Ala | Ile | Val |
| | | | | 100 | | | | | 105 | | | | | 110 | |
| Arg | Leu | Thr | Arg | Gln | Leu | Gln | Pro | Leu | Val | Tyr | Ser | Met | Met | Thr | Leu |
| | | | 115 | | | | | 120 | | | | | 125 | | |
| Leu | Val | Leu | Leu | Thr | Gly | Tyr | Ala | Leu | Leu | Ala | Arg | Arg | Asp | Arg | Pro |
| | 130 | | | | | 135 | | | | | 140 | | | | |
| Phe | Glu | Trp | His | Ile | Arg | His | Ala | Leu | Leu | Val | Ala | Val | Val | Thr | Ser |
| 145 | | | | | 150 | | | | | 155 | | | | | 160 |
| Leu | Ala | Leu | Ser | Pro | Asp | Arg | Tyr | Leu | Ser | Thr | Val | Val | Ala | Gly | Val |
| | | | | 165 | | | | | 170 | | | | | 175 | |
| Gln | Asp | Val | Ala | Gly | Trp | Leu | Ser | Gly | Pro | Trp | Thr | Ala | Pro | Asp | Gly |
| | | | | 180 | | | | | 185 | | | | | 190 | |
| Ala | Ala | Gly | Arg | Gly | Gly | Leu | Ala | Gln | Leu | Asp | Gln | Phe | Ala | Ala | Gln |
| | | | 195 | | | | | 200 | | | | | 205 | | |
| Ala | Gln | Ala | Trp | Val | Ala | Gln | Leu | Ala | Gly | Gln | Ala | Ala | Asn | Asp | Ala |
| | 210 | | | | | 215 | | | | | 220 | | | | |
| Asn | Pro | Gly | Ser | Ala | Val | Asn | Trp | Leu | Leu | Cys | Ala | Met | Ile | Val | Ala |
| 225 | | | | | 230 | | | | | 235 | | | | | 240 |
| Ala | Ser | Ala | Gly | Gly | Trp | Leu | Cys | Leu | Ala | Ala | Ser | Leu | Leu | Ile | Val |
| | | | | 245 | | | | | 250 | | | | | 255 | |
| Pro | Gly | Leu | Ile | Val | Thr | Leu | Leu | Leu | Ser | Leu | Gly | Pro | Leu | Phe | Leu |
| | | | | 260 | | | | | 265 | | | | | 270 | |

| | | | | | | | | | | | | | | | |
|---|---|---|---|---|---|---|---|---|---|---|---|---|---|---|---|
|Val|Leu|Leu 275|Leu|Phe|Pro|Ala|Leu 280|Gln|Arg|Trp|Thr|Asn 285|Ala|Trp|Leu|
|Gly|Ala 290|Leu|Val|Arg|Ala 295|Leu|Val|Phe|Met|Ala 300|Leu|Gly|Thr|Pro|Ala|
|Val 305|Gly|Leu|Leu|Ser|Asp 310|Val|Leu|Ala|Gly|Ala 315|Leu|Pro|Ala|Gly|Leu 320|
|Pro|Gln|Arg|Phe|Ala 325|Thr|Glu|Pro|Leu|Arg 330|Ser|Thr|Met|Leu|Ala 335|Ala|
|Thr|Leu|Cys|Ala 340|Thr|Ala|Thr|Leu|Met 345|Leu|Leu|Thr|Leu 350|Val|Pro|Leu|
|Ala|Ser|Ser 355|Val|Asn|Ala|Gly|Leu 360|Arg|Arg|Arg|Leu|Trp 365|Pro|Asn|Ala|
|Ala|His 370|Pro|Gly|Leu|Ala|Gln 375|Ala|His|Arg|Gln|Ala 380|Ala|Ala|Arg|Gln|
|Tyr 385|Ala|Arg|Arg|Pro|Ala 390|Ala|Ala|Ala|Ala|Ala 395|Ala|Gly|Pro|His|Gln 400|
|Ala|Gly|Thr|Tyr|Ala 405|Ala|Ser|Ala|Thr|Pro 410|Ala|Pro|Ala|Pro|Ala 415|Arg|
|Pro|Ala|Pro|Ser 420|Phe|Pro|Ala|His|Ala 425|Tyr|Arg|Gln|Tyr|Ala 430|Leu|Gly|
|Gly|Ala|Arg 435|Ser|Pro|Ala|Gly|Pro 440|Gly|Cys|Asp|Ala|Thr 445|Thr|Gly|Pro|
|Arg 450|Arg|Arg|Arg|Thr|Asp 455|Gly|Phe|Phe|Pro|Ala 460|Asn|Pro|Thr|Cys|His|
|Asp 465|Pro|Arg|Thr|Phe|Gln 470|Arg|Gln|Ile|Ile|Ala 475|Met|Gly|His|Pro|Gly 480|
|His|Arg|Pro|Arg|His 485|Ala|Arg|Arg|Leu|Arg 490|Pro|Glu|Ala|Gly|Arg 495|Pro|
|Ala|Cys|Arg|Ile 500|Pro|Met|Ala|Ser|Pro 505| | | | | | | |

(2) INFORMATION FOR SEQ ID NO:6:

(i) SEQUENCE CHARACTERISTICS:
        (A) LENGTH: 699 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..699

(xi) SEQUENCE DESCRIPTION: SEQ ID NO:6:

| | | | | | | | | | | | | | | | |
|---|---|---|---|---|---|---|---|---|---|---|---|---|---|---|---|
|ATG|CCA|GAC|CCG|CGC|CCC|TTG|ACG|CCT|GAC|CAG|ACG|CAT|GGC|CGC|GGG|
|Met 1|Pro|Asp|Pro|Arg 5|Pro|Leu|Thr|Pro|Asp 10|Gln|Thr|His|Gly|Arg 15|Gly|48|
|CAT|GCC|GAG|GCC|GCG|GTG|GAC|TGG|GAA|GCG|TCC|CGC|CTG|TAC|CGG|CTG|
|His|Ala|Glu|Ala 20|Ala|Val|Asp|Trp|Glu 25|Ala|Ser|Arg|Leu|Tyr 30|Arg|Leu|96|
|GCG|CAG|TCG|GAA|CGC|CGT|GCA|TGG|ACG|GTG|GCG|TGG|GCG|GCG|CTC|GCC|
|Ala|Gln|Ser 35|Glu|Arg|Arg|Ala|Trp 40|Thr|Val|Ala|Trp|Ala 45|Ala|Leu|Ala|144|
|GTG|ACC|GCG|CTG|TCA|TTG|ATC|GCC|ATC|GCG|ACG|ATG|CTT|CCG|CTC|AAG|
|Val|Thr 50|Ala|Leu|Ser|Leu|Ile 55|Ala|Ile|Ala|Thr|Met 60|Leu|Pro|Leu|Lys|192|
|ACC|ACC|ATT|CCT|TAC|CTG|ATC|GAG|GTC|GAA|AAG|AGC|AGC|GGC|GCG|GCC|240|

```
Thr  Thr  Ile  Pro  Tyr  Leu  Ile  Glu  Val  Glu  Lys  Ser  Ser  Gly  Ala  Ala
 65             70                       75                       80

TCG  GTC  GTC  ACG  CAA  TTC  GAA  CCC  CGA  GAT  TTC  ACC  CCG  GAC  ACC  TTG    288
Ser  Val  Val  Thr  Gln  Phe  Glu  Pro  Arg  Asp  Phe  Thr  Pro  Asp  Thr  Leu
                85                       90                       95

ATG  AAC  CAG  TAC  TGG  CTG  ACG  CGC  TAT  GTC  ACG  GCG  CGC  GAG  CGC  TAC    336
Met  Asn  Gln  Tyr  Trp  Leu  Thr  Arg  Tyr  Val  Thr  Ala  Arg  Glu  Arg  Tyr
               100                      105                      110

GAT  TGG  CAC  ACG  ATC  CAG  CAC  GAT  TAC  GAC  TAC  GTG  CGC  CTG  CTG  TCC    384
Asp  Trp  His  Thr  Ile  Gln  His  Asp  Tyr  Asp  Tyr  Val  Arg  Leu  Leu  Ser
          115                      120                      125

GCG  CCC  GCC  GTC  AGG  CAC  GAT  TAC  GAA  ACC  AGC  TAC  GAG  GCG  CCC  GAT    432
Ala  Pro  Ala  Val  Arg  His  Asp  Tyr  Glu  Thr  Ser  Tyr  Glu  Ala  Pro  Asp
     130                      135                      140

GCG  CCG  GAC  CGC  AAG  TAC  GGC  GCT  GGC  ACG  ACC  CTG  GCC  GTG  AAA  ATT    480
Ala  Pro  Asp  Arg  Lys  Tyr  Gly  Ala  Gly  Thr  Thr  Leu  Ala  Val  Lys  Ile
145                      150                      155                      160

CTC  AGC  GCC  ATC  GAC  CAT  GGC  AAG  GGC  GTC  GGC  ACG  GTG  CGC  TTT  GTC    528
Leu  Ser  Ala  Ile  Asp  His  Gly  Lys  Gly  Val  Gly  Thr  Val  Arg  Phe  Val
               165                      170                      175

CGG  ACA  CGG  CGC  GAC  GCG  GAC  GGG  CAG  GGC  GCC  GCC  GAA  TCC  TCG  ATA    576
Arg  Thr  Arg  Arg  Asp  Ala  Asp  Gly  Gln  Gly  Ala  Ala  Glu  Ser  Ser  Ile
               180                      185                      190

TGG  GTA  GCG  ACC  GTG  GCA  TTC  GCC  TAC  GAT  CAG  CCG  CGC  GCG  CTG  ACC    624
Trp  Val  Ala  Thr  Val  Ala  Phe  Ala  Tyr  Asp  Gln  Pro  Arg  Ala  Leu  Thr
          195                      200                      205

CAG  GCC  CAG  CGC  TGG  CTC  AAT  CCG  CTG  GGC  TTT  GCC  GTC  ACC  AGC  TAT    672
Gln  Ala  Gln  Arg  Trp  Leu  Asn  Pro  Leu  Gly  Phe  Ala  Val  Thr  Ser  Tyr
     210                      215                      220

CGC  GTC  GAC  GCG  GAG  GCT  GGA  CAG  CCA                                       699
Arg  Val  Asp  Ala  Glu  Ala  Gly  Gln  Pro
225                      230
```

( 2 ) INFORMATION FOR SEQ ID NO:7:

( i ) SEQUENCE CHARACTERISTICS:
        ( A ) LENGTH: 233 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met  Pro  Asp  Pro  Arg  Pro  Leu  Thr  Pro  Asp  Gln  Thr  His  Gly  Arg  Gly
  1             5                       10                       15

His  Ala  Glu  Ala  Ala  Val  Asp  Trp  Glu  Ala  Ser  Arg  Leu  Tyr  Arg  Leu
                20                       25                       30

Ala  Gln  Ser  Glu  Arg  Arg  Ala  Trp  Thr  Val  Ala  Trp  Ala  Ala  Leu  Ala
                35                       40                       45

Val  Thr  Ala  Leu  Ser  Leu  Ile  Ala  Ile  Ala  Thr  Met  Leu  Pro  Leu  Lys
      50                       55                       60

Thr  Thr  Ile  Pro  Tyr  Leu  Ile  Glu  Val  Glu  Lys  Ser  Ser  Gly  Ala  Ala
 65             70                       75                       80

Ser  Val  Val  Thr  Gln  Phe  Glu  Pro  Arg  Asp  Phe  Thr  Pro  Asp  Thr  Leu
                85                       90                       95

Met  Asn  Gln  Tyr  Trp  Leu  Thr  Arg  Tyr  Val  Thr  Ala  Arg  Glu  Arg  Tyr
               100                      105                      110

Asp  Trp  His  Thr  Ile  Gln  His  Asp  Tyr  Asp  Tyr  Val  Arg  Leu  Leu  Ser
          115                      120                      125

Ala  Pro  Ala  Val  Arg  His  Asp  Tyr  Glu  Thr  Ser  Tyr  Glu  Ala  Pro  Asp
```

```
                130                         135                             140
Ala   Pro   Asp   Arg   Lys   Tyr   Gly   Ala   Gly   Thr   Thr   Leu   Ala   Val   Lys   Ile
145                     150                       155                             160

Leu   Ser   Ala   Ile   Asp   His   Gly   Lys   Gly   Val   Gly   Thr   Val   Arg   Phe   Val
                  165                             170                       175

Arg   Thr   Arg   Arg   Asp   Ala   Asp   Gly   Gln   Gly   Ala   Ala   Glu   Ser   Ser   Ile
                  180                       185                             190

Trp   Val   Ala   Thr   Val   Ala   Phe   Ala   Tyr   Asp   Gln   Pro   Arg   Ala   Leu   Thr
                  195                       200                       205

Gln   Ala   Gln   Arg   Trp   Leu   Asn   Pro   Leu   Gly   Phe   Ala   Val   Thr   Ser   Tyr
      210                       215                             220

Arg   Val   Asp   Ala   Glu   Ala   Gly   Gln   Pro
225                     230
```

( 2 ) INFORMATION FOR SEQ ID NO:8:

( i ) SEQUENCE CHARACTERISTICS:
        ( A ) LENGTH: 819 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..819

( x i ) SEQUENCE DESCRIPTION: SEQ ID NO:8:

```
ATG   ATG   GCG   GCA   CGG   ATG   ATG   GCG   GCC   GGC   CTG   GCG   GCC   ACG   GCG   CTT        48
Met   Met   Ala   Ala   Arg   Met   Met   Ala   Ala   Gly   Leu   Ala   Ala   Thr   Ala   Leu
  1               5                       10                              15

TCG   GCG   CAT   GCG   TTC   CGG   ATA   CCC   ACG   CCA   GGA   GAA   CAG   GAC   GCC   CGC        96
Ser   Ala   His   Ala   Phe   Arg   Ile   Pro   Thr   Pro   Gly   Glu   Gln   Asp   Ala   Arg
                  20                              25                        30

ATA   CAG   ACC   GTG   CCG   TAC   CAC   CCG   GAG   GAG   GTG   GTG   CTG   GTG   CGC   GCC       144
Ile   Gln   Thr   Val   Pro   Tyr   His   Pro   Glu   Glu   Val   Val   Leu   Val   Arg   Ala
            35                              40                        45

TGG   AAC   GGC   TAC   GTC   ACC   CGG   ATC   GTA   TTC   GAC   GAG   CAG   GAG   AAG   ATC       192
Trp   Asn   Gly   Tyr   Val   Thr   Arg   Ile   Val   Phe   Asp   Glu   Gln   Glu   Lys   Ile
      50                              55                        60

ATC   GAC   GTC   GCC   GCG   GGG   TTC   GCC   GAC   GGC   TGG   CAA   TTC   AGC   CCG   GAA       240
Ile   Asp   Val   Ala   Ala   Gly   Phe   Ala   Asp   Gly   Trp   Gln   Phe   Ser   Pro   Glu
 65                     70                              75                              80

GGC   AAT   GTG   CTG   TAT   ATC   AAG   GCC   AAA   TCC   TTC   CCC   GCG   CAG   GGC   TCG       288
Gly   Asn   Val   Leu   Tyr   Ile   Lys   Ala   Lys   Ser   Phe   Pro   Ala   Gln   Gly   Ser
                        85                              90                        95

CCC   GCG   CAG   GCG   CCG   GAG   CCG   GGA   TTG   TGG   AAC   ACC   AAT   CTG   CTC   GTC       336
Pro   Ala   Gln   Ala   Pro   Glu   Pro   Gly   Leu   Trp   Asn   Thr   Asn   Leu   Leu   Val
            100                       105                             110

AAA   ACC   GAC   CGC   CGG   CTC   TAC   GAC   TTC   GAC   CTG   GTG   CTG   GCC   AGC   GCG       384
Lys   Thr   Asp   Arg   Arg   Leu   Tyr   Asp   Phe   Asp   Leu   Val   Leu   Ala   Ser   Ala
                  115                             120                       125

GAC   GCG   GCG   ACA   CCG   CAG   GCG   TTG   CAG   CGT   TCG   CGC   ATG   GCC   TAT   CGC       432
Asp   Ala   Ala   Thr   Pro   Gln   Ala   Leu   Gln   Arg   Ser   Arg   Met   Ala   Tyr   Arg
      130                       135                             140

CTG   CAA   TTC   CGC   TAC   CCG   GCC   GCG   CCG   CAG   GCG   GCA   TCC   CGC   GCC   AGC       480
Leu   Gln   Phe   Arg   Tyr   Pro   Ala   Ala   Pro   Gln   Ala   Ala   Ser   Arg   Ala   Ser
145                     150                             155                             160

CCC   GTC   GGC   CCG   GCT   GTT   CCC   GCC   GGC   GCA   TTG   AAC   CGG   CGC   TAC   GCC       528
Pro   Val   Gly   Pro   Ala   Val   Pro   Ala   Gly   Ala   Leu   Asn   Arg   Arg   Tyr   Ala
                        165                             170                       175
```

| | | | | | | | | | | | | | | | | |
|---|---|---|---|---|---|---|---|---|---|---|---|---|---|---|---|---|
| ATG | CAG | GTG | GGC | AAC | GGG | TCG | GAC | GGC | ATC | GCA | CCC | ATC | GCT | GCG | TAC | 576 |
| Met | Gln | Val | Gly | Asn | Gly | Ser | Asp | Gly | Ile | Ala | Pro | Ile | Ala | Ala | Tyr | |
| | | | 180 | | | | | 185 | | | | | 190 | | | |
| GAC | GAC | GGC | CGG | CAT | ACC | TGG | CTC | ACG | TTC | AGA | CCG | GGT | CAG | CCG | TTT | 624 |
| Asp | Asp | Gly | Arg | His | Thr | Trp | Leu | Thr | Phe | Arg | Pro | Gly | Gln | Pro | Phe | |
| | | 195 | | | | | 200 | | | | | 205 | | | | |
| CCG | GCC | GTA | TTC | GCG | GTA | GCG | CCG | GAC | GGA | ACG | GAA | ACC | CTG | GTC | AAT | 672 |
| Pro | Ala | Val | Phe | Ala | Val | Ala | Pro | Asp | Gly | Thr | Glu | Thr | Leu | Val | Asn | |
| | 210 | | | | | 215 | | | | | 220 | | | | | |
| CTG | CAT | ATC | GAC | AAC | CAA | TCA | CTG | GTC | ATA | CAC | CGG | GTA | GCG | CCG | GTC | 720 |
| Leu | His | Ile | Asp | Asn | Gln | Ser | Leu | Val | Ile | His | Arg | Val | Ala | Pro | Val | |
| 225 | | | | | 230 | | | | | 235 | | | | | 240 | |
| CTG | ATG | CTG | CGG | TCC | GGC | GCC | AGC | GTC | ATC | CGG | ATC | GTC | AAC | CAG | AAC | 768 |
| Leu | Met | Leu | Arg | Ser | Gly | Ala | Ser | Val | Ile | Arg | Ile | Val | Asn | Gln | Asn | |
| | | | | 245 | | | | | 250 | | | | | 255 | | |
| GGC | GAT | GCG | TCC | GAG | TCC | CCA | GCC | TTC | GAA | TGC | CAT | GCT | GAA | CCG | GCC | 816 |
| Gly | Asp | Ala | Ser | Glu | Ser | Pro | Ala | Phe | Glu | Cys | His | Ala | Glu | Pro | Ala | |
| | | | 260 | | | | | 265 | | | | | 270 | | | |
| CTC | | | | | | | | | | | | | | | | 819 |
| Leu | | | | | | | | | | | | | | | | |

( 2 ) INFORMATION FOR SEQ ID NO:9:

( i ) SEQUENCE CHARACTERISTICS:
        ( A ) LENGTH: 273 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| | | | | | | | | | | | | | | |
|---|---|---|---|---|---|---|---|---|---|---|---|---|---|---|
| Met | Met | Ala | Ala | Arg | Met | Met | Ala | Ala | Gly | Leu | Ala | Ala | Thr | Ala | Leu |
| 1 | | | | 5 | | | | | 10 | | | | | 15 |
| Ser | Ala | His | Ala | Phe | Arg | Ile | Pro | Thr | Pro | Gly | Glu | Gln | Asp | Ala | Arg |
| | | | 20 | | | | | 25 | | | | | 30 | | |
| Ile | Gln | Thr | Val | Pro | Tyr | His | Pro | Glu | Glu | Val | Val | Leu | Val | Arg | Ala |
| | | 35 | | | | | 40 | | | | | 45 | | | |
| Trp | Asn | Gly | Tyr | Val | Thr | Arg | Ile | Val | Phe | Asp | Glu | Gln | Glu | Lys | Ile |
| | 50 | | | | | 55 | | | | | 60 | | | | |
| Ile | Asp | Val | Ala | Ala | Gly | Phe | Ala | Asp | Gly | Trp | Gln | Phe | Ser | Pro | Glu |
| 65 | | | | | 70 | | | | | 75 | | | | | 80 |
| Gly | Asn | Val | Leu | Tyr | Ile | Lys | Ala | Lys | Ser | Phe | Pro | Ala | Gln | Gly | Ser |
| | | | | 85 | | | | | 90 | | | | | 95 | |
| Pro | Ala | Gln | Ala | Pro | Glu | Pro | Gly | Leu | Trp | Asn | Thr | Asn | Leu | Leu | Val |
| | | | 100 | | | | | 105 | | | | | 110 | | |
| Lys | Thr | Asp | Arg | Arg | Leu | Tyr | Asp | Phe | Asp | Leu | Val | Leu | Ala | Ser | Ala |
| | | 115 | | | | | 120 | | | | | 125 | | | |
| Asp | Ala | Ala | Thr | Pro | Gln | Ala | Leu | Gln | Arg | Ser | Arg | Met | Ala | Tyr | Arg |
| | 130 | | | | | 135 | | | | | 140 | | | | |
| Leu | Gln | Phe | Arg | Tyr | Pro | Ala | Ala | Pro | Gln | Ala | Ala | Ser | Arg | Ala | Ser |
| 145 | | | | | 150 | | | | | 155 | | | | | 160 |
| Pro | Val | Gly | Pro | Ala | Val | Pro | Ala | Gly | Ala | Leu | Asn | Arg | Arg | Tyr | Ala |
| | | | | 165 | | | | | 170 | | | | | 175 | |
| Met | Gln | Val | Gly | Asn | Gly | Ser | Asp | Gly | Ile | Ala | Pro | Ile | Ala | Ala | Tyr |
| | | | 180 | | | | | 185 | | | | | 190 | | |
| Asp | Asp | Gly | Arg | His | Thr | Trp | Leu | Thr | Phe | Arg | Pro | Gly | Gln | Pro | Phe |
| | | 195 | | | | | 200 | | | | | 205 | | | |
| Pro | Ala | Val | Phe | Ala | Val | Ala | Pro | Asp | Gly | Thr | Glu | Thr | Leu | Val | Asn |

|   |   |   |   |   |   |   |   |   |   |   |   |   |
|---|---|---|---|---|---|---|---|---|---|---|---|---|
|   |   |   | 210 |   |   |   | 215 |   |   |   | 220 |   |
| Leu | His | Ile | Asp | Asn | Gln | Ser | Leu | Val | Ile | His | Arg | Val | Ala | Pro | Val |
| 225 |   |   |   |   | 230 |   |   |   |   | 235 |   |   |   |   | 240 |
| Leu | Met | Leu | Arg | Ser | Gly | Ala | Ser | Val | Ile | Arg | Ile | Val | Asn | Gln | Asn |
|   |   |   |   | 245 |   |   |   |   | 250 |   |   |   |   | 255 |   |
| Gly | Asp | Ala | Ser | Glu | Ser | Pro | Ala | Phe | Glu | Cys | His | Ala | Glu | Pro | Ala |
|   |   |   | 260 |   |   |   |   | 265 |   |   |   |   | 270 |   |   |
| Leu |   |   |   |   |   |   |   |   |   |   |   |   |   |   |   |

( 2 ) INFORMATION FOR SEQ ID NO:10:

( i ) SEQUENCE CHARACTERISTICS:
        ( A ) LENGTH: 1152 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1152

( x i ) SEQUENCE DESCRIPTION: SEQ ID NO:10:

| ATG | CGT | CCG | AGT | CCC | CAG | CCT | TCG | AAT | GCC | ATG | CTG | AAC | CGG | CCC | TCT | 48 |
|---|---|---|---|---|---|---|---|---|---|---|---|---|---|---|---|---|
| Met | Arg | Pro | Ser | Pro | Gln | Pro | Ser | Asn | Ala | Met | Leu | Asn | Arg | Pro | Ser |   |
| 1 |   |   |   | 5 |   |   |   |   | 10 |   |   |   |   | 15 |   |   |
| AGT | CCC | GAT | GGC | GGC | GAA | GCG | CAC | GCT | TGG | CCG | CCG | GAC | CCC | GAA | ATC | 96 |
| Ser | Pro | Asp | Gly | Gly | Glu | Ala | His | Ala | Trp | Pro | Pro | Asp | Pro | Glu | Ile |   |
|   |   |   | 20 |   |   |   |   | 25 |   |   |   |   | 30 |   |   |   |
| CCT | GTT | TTC | GCC | AAT | GCC | GAG | CAT | GCG | CAT | CGG | CGT | CCG | CTG | CGC | TGG | 144 |
| Pro | Val | Phe | Ala | Asn | Ala | Glu | His | Ala | His | Arg | Arg | Pro | Leu | Arg | Trp |   |
|   |   | 35 |   |   |   |   | 40 |   |   |   |   | 45 |   |   |   |   |
| ATG | TTC | GCC | CTT | GTC | GCC | GTG | GCC | CTG | TCA | TGC | CTG | CTG | GCA | ACG | GGG | 192 |
| Met | Phe | Ala | Leu | Val | Ala | Val | Ala | Leu | Ser | Cys | Leu | Leu | Ala | Thr | Gly |   |
|   | 50 |   |   |   |   | 55 |   |   |   |   | 60 |   |   |   |   |   |
| ATA | TGG | CGC | AGC | CGC | GCC | GCG | CCG | CCG | CAC | GCC | GCG | ACG | CAG | ACC | GTC | 240 |
| Ile | Trp | Arg | Ser | Arg | Ala | Ala | Pro | Pro | His | Ala | Ala | Thr | Gln | Thr | Val |   |
| 65 |   |   |   |   | 70 |   |   |   |   | 75 |   |   |   |   | 80 |   |
| GCG | CCG | GCG | GGG | CAA | GCC | CTG | CCG | CCG | GGG | CGC | ATA | TTC | ACG | GTC | CAC | 288 |
| Ala | Pro | Ala | Gly | Gln | Ala | Leu | Pro | Pro | Gly | Arg | Ile | Phe | Thr | Val | His |   |
|   |   |   |   | 85 |   |   |   |   | 90 |   |   |   |   | 95 |   |   |
| CCA | CGC | GAA | CCC | GAA | CCG | GCG | CCG | CTT | CCG | GAC | ATG | CCG | GCG | GCT | CCC | 336 |
| Pro | Arg | Glu | Pro | Glu | Pro | Ala | Pro | Leu | Pro | Asp | Met | Pro | Ala | Ala | Pro |   |
|   |   |   | 100 |   |   |   |   | 105 |   |   |   |   | 110 |   |   |   |
| GAC | CCG | ATC | CTG | CCG | CAG | CCG | CGG | CCG | GCG | CCA | CCC | GTA | CCG | CCG | CCG | 384 |
| Asp | Pro | Ile | Leu | Pro | Gln | Pro | Arg | Pro | Ala | Pro | Pro | Val | Pro | Pro | Pro |   |
|   |   | 115 |   |   |   |   | 120 |   |   |   |   | 125 |   |   |   |   |
| CCA | ATC | CGC | GCG | CCG | TAC | GAC | TAC | GAT | GAA | CCG | GCG | CCC | CGG | CGC | GAC | 432 |
| Pro | Ile | Arg | Ala | Pro | Tyr | Asp | Tyr | Asp | Glu | Pro | Ala | Pro | Arg | Arg | Asp |   |
|   | 130 |   |   |   |   | 135 |   |   |   |   | 140 |   |   |   |   |   |
| AGC | GCG | GCG | CTC | AAG | TCC | GGC | CCG | GCC | ATG | ATG | GTC | GCC | ACG | GCC | GCG | 480 |
| Ser | Ala | Ala | Leu | Lys | Ser | Gly | Pro | Ala | Met | Met | Val | Ala | Thr | Ala | Ala |   |
| 145 |   |   |   |   | 150 |   |   |   |   | 155 |   |   |   |   | 160 |   |
| CGC | CTT | GGA | CAA | ACC | GAG | CGG | GCG | GGC | ATG | GCG | GAC | GAC | GGC | GTG | TCC | 528 |
| Arg | Leu | Gly | Gln | Thr | Glu | Arg | Ala | Gly | Met | Ala | Asp | Asp | Gly | Val | Ser |   |
|   |   |   |   | 165 |   |   |   |   | 170 |   |   |   |   | 175 |   |   |
| GCG | GAT | GCG | GCC | ACC | CTC | ATC | GGC | AGG | AAC | GTC | AGC | CGC | GCA | ACC | CGC | 576 |
| Ala | Asp | Ala | Ala | Thr | Leu | Ile | Gly | Arg | Asn | Val | Ser | Arg | Ala | Thr | Arg |   |
|   |   |   | 180 |   |   |   |   | 185 |   |   |   |   | 190 |   |   |   |
| TCC | GGG | GGC | CGC | GAT | TAC | CGG | CTG | CTG | CCC | GGC | ACG | TTT | ATC | GAT | TGC | 624 |
| Ser | Gly | Gly | Arg | Asp | Tyr | Arg | Leu | Leu | Pro | Gly | Thr | Phe | Ile | Asp | Cys |   |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 195 |     |     |     | 200 |     |     |     |     | 205 |     |     |     |      |
| ATC | CTG | CAG | ACC | CGG | ATC | GTC | ACC | AAC | GTC | CCG | GGG | CTG | ACG | ACC | TGC | 672  |
| Ile | Leu | Gln | Thr | Arg | Ile | Val | Thr | Asn | Val | Pro | Gly | Leu | Thr | Thr | Cys |      |
|     |     | 210 |     |     |     | 215 |     |     |     |     | 220 |     |     |     |     |      |
| ATC | GTA | TCG | CGG | GAT | GTC | TAC | AGC | GCC | AGC | GGC | AAG | CGC | GTC | CTG | GTG | 720  |
| Ile | Val | Ser | Arg | Asp | Val | Tyr | Ser | Ala | Ser | Gly | Lys | Arg | Val | Leu | Val |      |
| 225 |     |     |     |     | 230 |     |     |     |     | 235 |     |     |     |     | 240 |      |
| CCG | CGT | GGC | ACG | ACA | GTG | GTG | GGC | GAA | TAC | CGC | GCC | GAC | CTG | GCG | CAG | 768  |
| Pro | Arg | Gly | Thr | Thr | Val | Val | Gly | Glu | Tyr | Arg | Ala | Asp | Leu | Ala | Gln |      |
|     |     |     |     | 245 |     |     |     |     | 250 |     |     |     |     | 255 |     |      |
| GGC | TCG | CAA | CGC | ATC | TAC | GTC | GCA | TGG | AGC | CGG | CTT | TTC | ATG | CCG | TCC | 816  |
| Gly | Ser | Gln | Arg | Ile | Tyr | Val | Ala | Trp | Ser | Arg | Leu | Phe | Met | Pro | Ser |      |
|     |     |     | 260 |     |     |     |     | 265 |     |     |     |     | 270 |     |     |      |
| GGG | CTC | ACG | ATA | GAG | CTG | GCA | TCG | CCG | GCC | GTG | GAC | GGA | ACC | GGC | GCC | 864  |
| Gly | Leu | Thr | Ile | Glu | Leu | Ala | Ser | Pro | Ala | Val | Asp | Gly | Thr | Gly | Ala |      |
|     |     | 275 |     |     |     |     | 280 |     |     |     |     | 285 |     |     |     |      |
| GCG | GGG | CTG | CCC | GGC | GTG | GTG | GAC | GAC | AAA | TTC | GCG | CAG | CGT | TTC | GGC | 912  |
| Ala | Gly | Leu | Pro | Gly | Val | Val | Asp | Asp | Lys | Phe | Ala | Gln | Arg | Phe | Gly |      |
|     | 290 |     |     |     |     | 295 |     |     |     |     | 300 |     |     |     |     |      |
| GGC | GCC | CTG | CTG | CTG | AGC | GTA | TTG | GGC | GAT | GCC | ACC | TCG | TAC | ATG | CTG | 960  |
| Gly | Ala | Leu | Leu | Leu | Ser | Val | Leu | Gly | Asp | Ala | Thr | Ser | Tyr | Met | Leu |      |
| 305 |     |     |     |     | 310 |     |     |     |     | 315 |     |     |     |     | 320 |      |
| GCG | CGC | GCC | ACC | GAT | GCG | CGC | CAC | GGC | GTG | AAC | GTG | AAC | CTT | ACC | GCC | 1008 |
| Ala | Arg | Ala | Thr | Asp | Ala | Arg | His | Gly | Val | Asn | Val | Asn | Leu | Thr | Ala |      |
|     |     |     |     | 325 |     |     |     |     | 330 |     |     |     |     | 335 |     |      |
| GCG | GGA | ACG | ATG | AAT | TCG | CTG | GCC | GCC | AGC | GCC | CTG | AAC | AAC | ACG | ATC | 1056 |
| Ala | Gly | Thr | Met | Asn | Ser | Leu | Ala | Ala | Ser | Ala | Leu | Asn | Asn | Thr | Ile |      |
|     |     |     | 340 |     |     |     |     | 345 |     |     |     |     | 350 |     |     |      |
| AAC | ATC | CCG | CCC | ACG | CTC | TAC | AAG | AAC | CAC | GGC | GAC | CAG | ATC | GGC | ATC | 1104 |
| Asn | Ile | Pro | Pro | Thr | Leu | Tyr | Lys | Asn | His | Gly | Asp | Gln | Ile | Gly | Ile |      |
|     |     |     | 355 |     |     |     |     | 360 |     |     |     |     | 365 |     |     |      |
| CTG | GTC | GCC | CGT | CCA | TTG | GAC | TTC | TCC | ATA | CTC | AGG | GGG | ACG | AAT | GAA | 1152 |
| Leu | Val | Ala | Arg | Pro | Leu | Asp | Phe | Ser | Ile | Leu | Arg | Gly | Thr | Asn | Glu |      |
|     |     |     | 370 |     |     |     |     | 375 |     |     |     |     | 380 |     |     |      |

( 2 ) INFORMATION FOR SEQ ID NO:11:

( i ) SEQUENCE CHARACTERISTICS:
        ( A ) LENGTH: 384 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Arg | Pro | Ser | Pro | Gln | Pro | Ser | Asn | Ala | Met | Leu | Asn | Arg | Pro | Ser |
| 1   |     |     |     | 5   |     |     |     |     | 10  |     |     |     |     | 15  |     |
| Ser | Pro | Asp | Gly | Gly | Glu | Ala | His | Ala | Trp | Pro | Pro | Asp | Pro | Glu | Ile |
|     |     |     | 20  |     |     |     |     | 25  |     |     |     |     | 30  |     |     |
| Pro | Val | Phe | Ala | Asn | Ala | Glu | His | Ala | His | Arg | Arg | Pro | Leu | Arg | Trp |
|     |     | 35  |     |     |     |     | 40  |     |     |     |     | 45  |     |     |     |
| Met | Phe | Ala | Leu | Val | Ala | Val | Ala | Leu | Ser | Cys | Leu | Leu | Ala | Thr | Gly |
|     | 50  |     |     |     |     | 55  |     |     |     |     | 60  |     |     |     |     |
| Ile | Trp | Arg | Ser | Arg | Ala | Ala | Pro | Pro | His | Ala | Thr | Gln | Thr | Val |
| 65  |     |     |     |     | 70  |     |     |     |     | 75  |     |     |     |     | 80  |
| Ala | Pro | Ala | Gly | Gln | Ala | Leu | Pro | Pro | Gly | Arg | Ile | Phe | Thr | Val | His |
|     |     |     |     | 85  |     |     |     |     | 90  |     |     |     |     | 95  |     |
| Pro | Arg | Glu | Pro | Glu | Pro | Ala | Pro | Leu | Pro | Asp | Met | Pro | Ala | Ala | Pro |
|     |     |     | 100 |     |     |     |     | 105 |     |     |     |     | 110 |     |     |
| Asp | Pro | Ile | Leu | Pro | Gln | Pro | Arg | Pro | Ala | Pro | Pro | Val | Pro | Pro | Pro |

|     |     |     | 115 |     |     |     | 120 |     |     |     | 125 |     |     |     |
|-----|-----|-----|-----|-----|-----|-----|-----|-----|-----|-----|-----|-----|-----|-----|

Pro Ile Arg Ala Pro Tyr Asp Tyr Asp Glu Pro Ala Pro Arg Arg Asp
    130                        135                    140

Ser Ala Ala Leu Lys Ser Gly Pro Ala Met Met Val Ala Thr Ala Ala
145                      150                155                    160

Arg Leu Gly Gln Thr Glu Arg Ala Gly Met Ala Asp Asp Gly Val Ser
                165                170                175

Ala Asp Ala Ala Thr Leu Ile Gly Arg Asn Val Ser Arg Ala Thr Arg
            180                  185              190

Ser Gly Gly Arg Asp Tyr Arg Leu Leu Pro Gly Thr Phe Ile Asp Cys
        195              200                205

Ile Leu Gln Thr Arg Ile Val Thr Asn Val Pro Gly Leu Thr Thr Cys
    210                  215              220

Ile Val Ser Arg Asp Val Tyr Ser Ala Ser Gly Lys Arg Val Leu Val
225                    230              235                240

Pro Arg Gly Thr Thr Val Val Gly Glu Tyr Arg Ala Asp Leu Ala Gln
            245                250              255

Gly Ser Gln Arg Ile Tyr Val Ala Trp Ser Arg Leu Phe Met Pro Ser
        260              265              270

Gly Leu Thr Ile Glu Leu Ala Ser Pro Ala Val Asp Gly Thr Gly Ala
    275                  280              285

Ala Gly Leu Pro Gly Val Val Asp Asp Lys Phe Ala Gln Arg Phe Gly
    290                  295              300

Gly Ala Leu Leu Leu Ser Val Leu Gly Asp Ala Thr Ser Tyr Met Leu
305                    310              315                320

Ala Arg Ala Thr Asp Ala Arg His Gly Val Asn Val Asn Leu Thr Ala
            325                330              335

Ala Gly Thr Met Asn Ser Leu Ala Ala Ser Ala Leu Asn Asn Thr Ile
            340                345              350

Asn Ile Pro Pro Thr Leu Tyr Lys Asn His Gly Asp Gln Ile Gly Ile
        355              360                365

Leu Val Ala Arg Pro Leu Asp Phe Ser Ile Leu Arg Gly Thr Asn Glu
    370                  375              380

( 2 ) INFORMATION FOR SEQ ID NO:12:

( i ) SEQUENCE CHARACTERISTICS:
        ( A ) LENGTH: 951 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..951

( x i ) SEQUENCE DESCRIPTION: SEQ ID NO:12:

```
ATG  AAT  GAT  GCC  GCG  CCG  GAT  CGA  CAG  GCA  TCG  GTC  GAC  TTC  CAC  CTC        48
Met  Asn  Asp  Ala  Ala  Pro  Asp  Arg  Gln  Ala  Ser  Val  Asp  Phe  His  Leu
 1                  5                        10                       15

CAA  GCG  CTG  CAT  CCG  TGG  CTG  AGC  CGG  CAG  GAT  ATA  GCG  GAA  ATC  TGC        96
Gln  Ala  Leu  His  Pro  Trp  Leu  Ser  Arg  Gln  Asp  Ile  Ala  Glu  Ile  Cys
                20                       25                       30

GTG  AAC  CGT  CCG  GGG  CAG  CTC  TGG  TAT  GAA  GAC  CGC  AAC  GGC  TGG  AAC       144
Val  Asn  Arg  Pro  Gly  Gln  Leu  Trp  Tyr  Glu  Asp  Arg  Asn  Gly  Trp  Asn
           35                       40                       45

CGC  CAG  GAG  TCG  GGC  GCG  CTC  ACG  CTT  GAT  CAT  CTG  CAC  GCC  CTG  GCT       192
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Arg | Gln | Glu | Ser | Gly | Ala | Leu | Thr | Leu | Asp | His | Leu | His | Ala | Leu | Ala |     |
|     | 50  |     |     |     | 55  |     |     |     |     | 60  |     |     |     |     |     |     |
| ACC | GCG | ACG | GCC | CGG | TTC | TGC | GAC | CGC | GAC | ATT | TGC | CCG | GAG | CGT | CCC | 240 |
| Thr | Ala | Thr | Ala | Arg | Phe | Cys | Asp | Arg | Asp | Ile | Cys | Pro | Glu | Arg | Pro |     |
| 65  |     |     |     |     | 70  |     |     |     |     | 75  |     |     |     |     | 80  |     |
| TTG | CTG | GCG | GCG | TCC | CTG | CCT | GGC | GGC | GAA | CGG | GTG | CAG | ATC | GTC | GTC | 288 |
| Leu | Leu | Ala | Ala | Ser | Leu | Pro | Gly | Gly | Glu | Arg | Val | Gln | Ile | Val | Val |     |
|     |     |     |     | 85  |     |     |     |     | 90  |     |     |     |     | 95  |     |     |
| CCT | CCA | GCC | TGC | GAA | CCG | GGC | ACG | CTG | TCG | CTG | ACC | ATC | CGC | AAG | CCC | 336 |
| Pro | Pro | Ala | Cys | Glu | Pro | Gly | Thr | Leu | Ser | Leu | Thr | Ile | Arg | Lys | Pro |     |
|     |     |     | 100 |     |     |     |     | 105 |     |     |     |     | 110 |     |     |     |
| GCC | CGG | CGC | ATC | TGG | CCA | CTA | TCG | GAA | CTG | TTG | CGC | GAT | ACG | CTC | GAC | 384 |
| Ala | Arg | Arg | Ile | Trp | Pro | Leu | Ser | Glu | Leu | Leu | Arg | Asp | Thr | Leu | Asp |     |
|     |     | 115 |     |     |     |     | 120 |     |     |     |     | 125 |     |     |     |     |
| CTG | CCA | GGC | GTC | CCG | GGC | GCC | AGC | CAA | GCG | CGG | CCA | GAC | CCC | TTG | CTC | 432 |
| Leu | Pro | Gly | Val | Pro | Gly | Ala | Ser | Gln | Ala | Arg | Pro | Asp | Pro | Leu | Leu |     |
|     | 130 |     |     |     |     | 135 |     |     |     |     | 140 |     |     |     |     |     |
| GAC | CCG | TGG | AGG | CGC | GGC | GCA | TGG | GAC | GAC | TTC | CTG | CGG | CTG | GCC | GTG | 480 |
| Asp | Pro | Trp | Arg | Arg | Gly | Ala | Trp | Asp | Asp | Phe | Leu | Arg | Leu | Ala | Val |     |
| 145 |     |     |     |     | 150 |     |     |     |     | 155 |     |     |     |     | 160 |     |
| CAG | GCG | GGC | AAG | GCC | ATA | CTC | GTC | GCC | GGC | CAG | ACC | GGT | TCG | GGC | AAG | 528 |
| Gln | Ala | Gly | Lys | Ala | Ile | Leu | Val | Ala | Gly | Gln | Thr | Gly | Ser | Gly | Lys |     |
|     |     |     |     | 165 |     |     |     |     | 170 |     |     |     |     | 175 |     |     |
| ACC | ACA | TTG | ATG | AAC | GCG | TTG | AGC | GGG | GAG | ATT | CCG | CCC | CGC | GAA | CGC | 576 |
| Thr | Thr | Leu | Met | Asn | Ala | Leu | Ser | Gly | Glu | Ile | Pro | Pro | Arg | Glu | Arg |     |
|     |     |     | 180 |     |     |     |     | 185 |     |     |     |     | 190 |     |     |     |
| ATC | GTC | ACG | ATC | GAG | GAC | GTG | CGC | GAG | TTG | CGG | CTG | GAT | CCG | GCA | ACC | 624 |
| Ile | Val | Thr | Ile | Glu | Asp | Val | Arg | Glu | Leu | Arg | Leu | Asp | Pro | Ala | Thr |     |
|     |     | 195 |     |     |     |     | 200 |     |     |     |     | 205 |     |     |     |     |
| AAT | CAC | GTA | CAC | CTG | TTG | TTC | GGC | ACT | CCT | ACG | GAA | GGC | AGG | ACG | GCC | 672 |
| Asn | His | Val | His | Leu | Leu | Phe | Gly | Thr | Pro | Thr | Glu | Gly | Arg | Thr | Ala |     |
|     | 210 |     |     |     |     | 215 |     |     |     |     | 220 |     |     |     |     |     |
| GCC | GTA | TCG | GCC | ACC | GAG | CTG | TTG | CGC | GCG | GCG | CTG | CGC | ATG | GCG | CCC | 720 |
| Ala | Val | Ser | Ala | Thr | Glu | Leu | Leu | Arg | Ala | Ala | Leu | Arg | Met | Ala | Pro |     |
| 225 |     |     |     |     | 230 |     |     |     |     | 235 |     |     |     |     | 240 |     |
| ACG | CGC | ATC | CTG | CTG | GCG | GAG | CTG | CGC | GGG | GGA | GAA | GCC | TTC | GAC | TTC | 768 |
| Thr | Arg | Ile | Leu | Leu | Ala | Glu | Leu | Arg | Gly | Gly | Glu | Ala | Phe | Asp | Phe |     |
|     |     |     |     | 245 |     |     |     |     | 250 |     |     |     |     | 255 |     |     |
| CTC | CAG | GCA | TGC | GCG | TCC | GGA | CAC | AGC | GGC | GGC | ATC | AGC | ACC | TGC | CAT | 816 |
| Leu | Gln | Ala | Cys | Ala | Ser | Gly | His | Ser | Gly | Gly | Ile | Ser | Thr | Cys | His |     |
|     |     |     | 260 |     |     |     |     | 265 |     |     |     |     | 270 |     |     |     |
| GCC | GCC | AGC | GCC | GAT | ATG | GCG | CTG | CAG | CGG | CTG | ACG | CTG | ATG | TGC | ATG | 864 |
| Ala | Ala | Ser | Ala | Asp | Met | Ala | Leu | Gln | Arg | Leu | Thr | Leu | Met | Cys | Met |     |
|     |     | 275 |     |     |     |     | 280 |     |     |     |     | 285 |     |     |     |     |
| CAA | CAC | CCG | AAT | TGC | CAG | ATG | CTT | CCC | TAC | TCG | ACG | CTA | CGC | GCG | CTG | 912 |
| Gln | His | Pro | Asn | Cys | Gln | Met | Leu | Pro | Tyr | Ser | Thr | Leu | Arg | Ala | Leu |     |
|     | 290 |     |     |     |     | 295 |     |     |     |     | 300 |     |     |     |     |     |
| GTC | GAA | TCC | GTG | ATC | GAT | ACT | CTA | GAG | GAT | TCG | GCC | GGG |     |     |     | 951 |
| Val | Glu | Ser | Val | Ile | Asp | Thr | Leu | Glu | Asp | Ser | Ala | Gly |     |     |     |     |
| 305 |     |     |     |     | 310 |     |     |     |     | 315 |     |     |     |     |     |     |

( 2 ) INFORMATION FOR SEQ ID NO:13:

( i ) SEQUENCE CHARACTERISTICS:
( A ) LENGTH: 317 amino acids
( B ) TYPE: amino acid
( D ) TOPOLOGY: linear ( i i ) MOLECULE TYPE: protein ( x i ) SEQUENCE DESCRIPTION: SEQ ID NO:13:

Met Asn Asp Ala Ala Pro Asp Arg Gln Ala Ser Val Asp Phe His Leu

-continued

```
  1                     5                          10                          15

Gln  Ala  Leu  His  Pro  Trp  Leu  Ser  Arg  Gln  Asp  Ile  Ala  Glu  Ile  Cys
               20                      25                     30

Val  Asn  Arg  Pro  Gly  Gln  Leu  Trp  Tyr  Glu  Asp  Arg  Asn  Gly  Trp  Asn
               35                      40                     45

Arg  Gln  Glu  Ser  Gly  Ala  Leu  Thr  Leu  Asp  His  Leu  His  Ala  Leu  Ala
          50                      55                     60

Thr  Ala  Thr  Ala  Arg  Phe  Cys  Asp  Arg  Asp  Ile  Cys  Pro  Glu  Arg  Pro
     65                      70                     75                     80

Leu  Leu  Ala  Ala  Ser  Leu  Pro  Gly  Gly  Glu  Arg  Val  Gln  Ile  Val  Val
                    85                      90                          95

Pro  Pro  Ala  Cys  Glu  Pro  Gly  Thr  Leu  Ser  Leu  Thr  Ile  Arg  Lys  Pro
               100                     105                    110

Ala  Arg  Arg  Ile  Trp  Pro  Leu  Ser  Glu  Leu  Leu  Arg  Asp  Thr  Leu  Asp
          115                     120                    125

Leu  Pro  Gly  Val  Pro  Gly  Ala  Ser  Gln  Ala  Arg  Pro  Asp  Pro  Leu  Leu
     130                     135                    140

Asp  Pro  Trp  Arg  Arg  Gly  Ala  Trp  Asp  Asp  Phe  Leu  Arg  Leu  Ala  Val
145                      150                    155                         160

Gln  Ala  Gly  Lys  Ala  Ile  Leu  Val  Ala  Gly  Gln  Thr  Gly  Ser  Gly  Lys
                    165                     170                         175

Thr  Thr  Leu  Met  Asn  Ala  Leu  Ser  Gly  Glu  Ile  Pro  Pro  Arg  Glu  Arg
               180                     185                    190

Ile  Val  Thr  Ile  Glu  Asp  Val  Arg  Glu  Leu  Arg  Leu  Asp  Pro  Ala  Thr
          195                     200                    205

Asn  His  Val  His  Leu  Leu  Phe  Gly  Thr  Pro  Thr  Glu  Gly  Arg  Thr  Ala
     210                     215                    220

Ala  Val  Ser  Ala  Thr  Glu  Leu  Leu  Arg  Ala  Ala  Leu  Arg  Met  Ala  Pro
225                      230                    235                         240

Thr  Arg  Ile  Leu  Leu  Ala  Glu  Leu  Arg  Gly  Gly  Glu  Ala  Phe  Asp  Phe
               245                     250                         255

Leu  Gln  Ala  Cys  Ala  Ser  Gly  His  Ser  Gly  Gly  Ile  Ser  Thr  Cys  His
               260                     265                    270

Ala  Ala  Ser  Ala  Asp  Met  Ala  Leu  Gln  Arg  Leu  Thr  Leu  Met  Cys  Met
          275                     280                    285

Gln  His  Pro  Asn  Cys  Gln  Met  Leu  Pro  Tyr  Ser  Thr  Leu  Arg  Ala  Leu
     290                     295                    300

Val  Glu  Ser  Val  Ile  Asp  Thr  Leu  Glu  Asp  Ser  Ala  Gly
305                 310                     315
```

GENES FOR THE EXPORT OF *PERTUSSIS* HOLOTOXIN

RELATED APPLICATION

This application is a continuation-in-part of U.S. patent application Ser. No. 08/031,619, filed March 15, 1993 now abandoned, the teachings of which are incorporated herein by reference.

BACKGROUND OF THE INVENTION

*Bordetella pertussis* is the primary causative agent of pertussis, or whooping cough, an acute infection of the respiratory tract. Pertussis occurs worldwide and is most severe when it infects unimmunized infants. Currently available vaccines (whole cell and partially purified acellular) are believed to have approximately 80–90% efficacy in the first few years after immunization. Effective immunization declines, in the case of whole cell vaccines, to almost no efficacy by 12 years postimmunization. The duration of protection provided by the acellular vaccine is unknown. The currently available vaccines are accompanied by a number of adverse reactions, some of which are severe or life-threatening. These severe reactions can include high fever, seizures, a shock-like hypo responsive state, encephalopathy and severe allergic reactions. In addition, individuals completely immunized with these vaccines can still develop pertussis. A purified component vaccine specific to the pertussis holotoxin would be useful for developing specific immunity to *B. pertussis* while minimizing potential adverse side effects caused by the currently available complex whole-cell or partially purified acellular vaccines.

One of the limitations of a purified component *B. Pertussis* vaccine is the time and expense involved in the growth and processing of large fermentor volumes of *B. pertussis* required to obtain sufficient amounts of pertussis holotoxin (PT) or mutated forms of the toxin protein, known as cross reactive materials or CRMs. Several investigators have attempted to overcome this limitation by over expression of PT using either homologous expression systems in *B. pertussis*, or in closely related *B. parapertussis* or *B. bronchiseptica* species (Lee, C. K. et al., *Infect. Immun.* 57:1413–1418 (1989)), or by utilizing heterologous expression systems such as *E. coli* or *B. subtilis* (Burnette, W. N. et al., *Bio/Technology* 699–705 (1988); Locht, C. and J. M. Keith, *Science* 232:1258–1264 (1986); Nicosia, A., et al., *Proc. Natl. Acad. Sci. USA* 83:4631 (1986)). Unfortunately, these efforts have failed to provide any system capable of consistently yielding amounts of PT holotoxin significantly greater than the amount obtained from cultures of wild type *B. pertussis*.

SUMMARY OF THE INVENTION

The present invention is based upon the identification of a cloned region of the *B. pertussis* genome. This includes a purified or partially purified nucleic acid sequence comprising an approximately 8 kb region of the *B. pertussis* genome, defined herein as the pts region, located immediately 3' (downstream) of the *B. pertussis* ptx operon. This cloned region encodes factors required for efficient expression and secretion of pertussis holotoxin. The nucleic acid sequence comprises at least six genes, designated ptsAB (SEQ ID NO: 2), ptsC (SEQ ID NO: 4), ptsD (SEQ ID NO: 6), ptsE (SEQ ID NO: 8), ptsF (SEQ ID NO: 10) and ptsG (SEQ ID NO: 12), (encoding polypeptides SEQ ID NO: 3, SEQ ID NO: 5, SEQ ID NO: 7, SEQ ID NO: 9, SEQ ID NO:11 and SEQ ID NO: 13, respectively) consisting essentially of the nucleotide sequence as shown in and SEQ ID NO: 1. Nucleic acid sequences complementary to all or a portion of the sequence described by SEQ ID NO: 1 and nucleic acid sequences which hybridize under stringent conditions to all or a portion of the sequence described by SEQ ID NO: 1 or its complement are also embraced by the present invention.

A nucleic acid sequence comprising an approximately 4.5 kb region of the *B. pertussis* genome 3' of and contiguous with the approximately 8 kb region 3' of ptx has been isolated and identified. This region, represented by the restriction map shown in FIGS. 1 and 2B, is also described.

In addition to the cloned *B. pertussis* sequences described herein, the present invention includes plasmid constructs comprising the cloned *B. pertussis* sequences, as well as hosts harboring these plasmid constructs. These constructs contain both the approximately 8 kb region of the *B. pertussis* genome 3' of the ptx operon, and the approximately 4.5 kb region further 3' and contiguous with the 8 kb region.

In another embodiment, the present invention includes methods for achieving expression and secretion of *B. pertussis* holotoxin in a homologous or heterologous host. According to this embodiment, regions of pts necessary or useful for expression and/or secretion of holotoxin in a heterologous host are introduced into the heterologous host in combination with the ptx region encoding *B. pertussis* holotoxin. The host is then maintained under conditions suitable for expression and secretion of holotoxin. Using this method expression and/or secretion of holotoxin can be regulated (e.g., up or down regulated) by, for example, placing one or more regions of pts under the transcriptional control of a heterologous promoter, increasing pts and ptx gene dosage, or improving the activity of transcriptional activators of ptx, such as BvgA. These methods of regulating expression and/or secretion of holotoxin can be used to produce over expressing strains of *B. pertussis*, or to produce overproducing heterologous strains.

A further embodiment of the present invention includes methods for producing large quantities of *B. pertussis* holotoxin for use in vaccine production. These methods include growth of a ptx over expressing strain of *B. pertussis*, followed by purification of the holotoxin from the medium. Also included is holotoxin production employing a more rapidly growing and/or over expressing homologous or heterologous host strain containing ptx under the control of a heterologous promoter (e.g., tac) and regions of pts necessary or useful for expression and secretion of holotoxin from the host strain. Growth of the host strain is then followed by isolation of holotoxin from the growth medium.

BRIEF DESCRIPTION OF THE DRAWINGS

FIG. 1 is a restriction map of the plasmid pPX2557 containing *B. pertussis* genomic DNA 3' of the ptx operon.

FIG. 3 is a schematic depiction of the *B. pertussis* ptsA and ptsB region mutants and cloned mutant genomic sequences.

DETAILED DESCRIPTION OF THE INVENTION

Figure 2A:
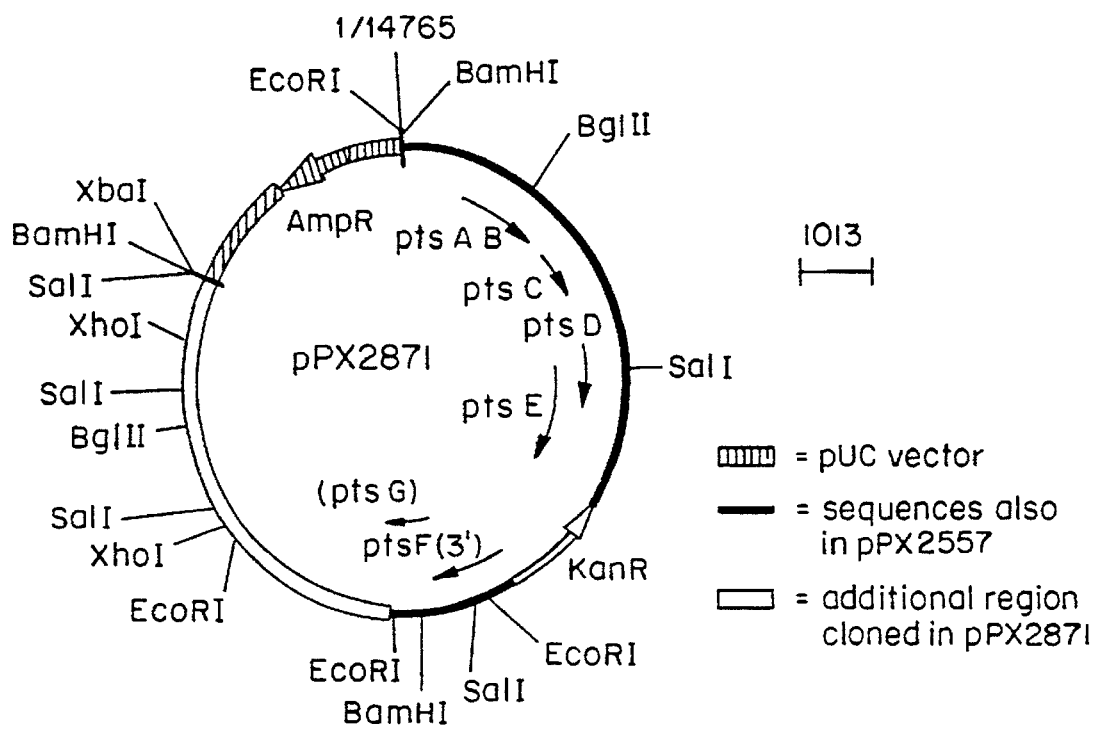
FIG. 2A is a restriction map of pPX2871 containing *B. pertussis* chromosomal sequences 3' of the sequences cloned in pPX2557. The gene designated ptsAB (SEQ ID NO: 2) does not contain the first 685 base pairs of the coding region.
Figure 2B:
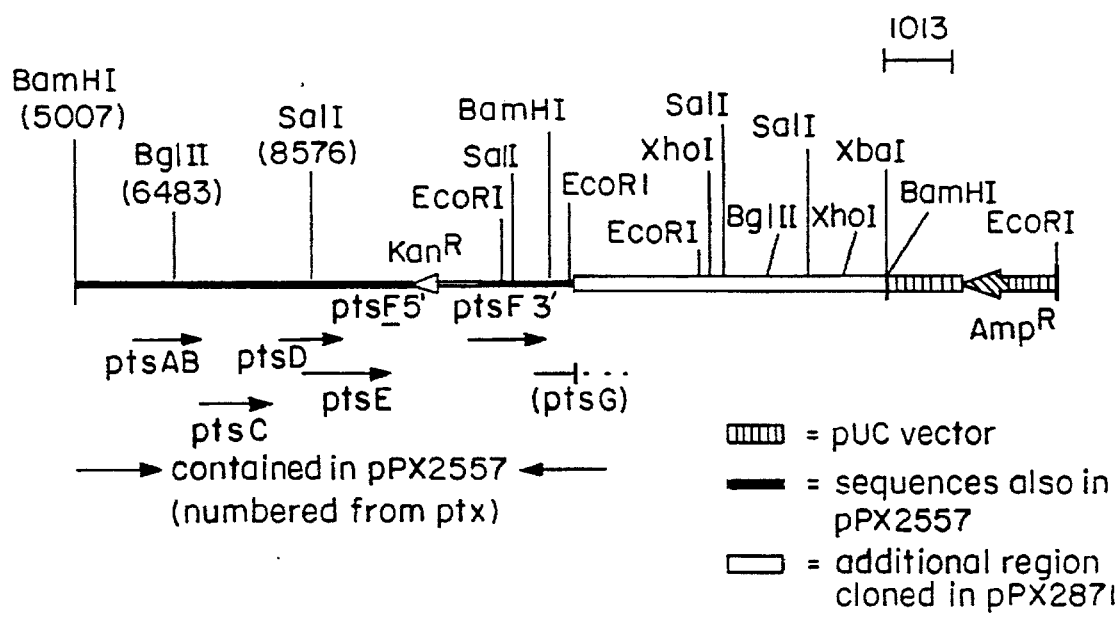
FIG. 2B is a linear restriction map of the *B. pertussis* genomic region cloned in pPX2871 (open box) showing the approximate locations of selected restriction sites numbered from the beginning of the cloned ptx sequences (the numbering omitting the approximately 1.2 kb contributed by the Kan$^r$ gene insert). The gene designated pts AB does not contain the first 685 base pairs of the coding region.

A portion of the *B. pertussis* genome encoding products essential for transcription of the genes encoding the hexameric pertussis holotoxin (referred to as PT or holotoxin), and extracellular export of assembled holotoxin has been cloned and characterized. The cloned portion of the genome is located downstream (3') of ptx (the region encoding holotoxin subunits) and extends from approximately base 4322 (base 1 is defined as the beginning of ptx sequences) to approximately base 16471. This region is cloned in two plasmids, pPX2557 and pPX2871. pPX2557 is shown in FIG. 1 and includes previously characterized nucleic acid sequences (Nicosia, A. et al., *Proc. Natl. Acad. Sci. USA* 83:4631–4635 (1986)) from the beginning of ptx extending into the beginning of an open reading frame designated herein as ptsAB (SEQ ID NO: 2). pPX2557 also includes a previously unreported region of the *B. pertussis* genome extending 3' through the rest of ptsAB and through at least 4 more complete open reading frames (designated ptsC (SEQ ID NO: 4), ptsD (SEQ ID NO: 6), ptsE (SEQ ID NO: 8)and ptsF (SEQ ID NO: 10)) and includes an incomplete open reading frame (ptsG (SEQ ID NO: 12)) ending at approximately base 12064. In the restriction map of plasmid pPX2557 shown in FIG. 1, the dark filled regions represent the ptx operon and the cloned 3' region of the *B. pertussis* . Unfilled regions represent either pUC vector DNA or the kanamycin resistance ($Kan^r$ ) gene (from pUC4K) used to disrupt the chromosomal ptx S1 gene of the strain used as a source of DNA for the cloning. Other symbols depict the pertussis toxin subunits (S2–S5), the ptx promoter ($P_{ptx}$), the ptsAB gene (SEQ ID NO: 2), and open reading frames designated ptsC (SEQ ID NO: 4), ptsD (SEQ ID NO: 6), ptsE (SEQ ID NO: 8), ptsF (SEQ ID NO: 10)and ptsG (SEQ ID NO: 12). Previously unpublished sequence data extends from the EcoRI site at 4931 to the site at position 12064.

Plasmid pPX2871 is shown in FIG. 2A and includes the last approximately 6876 bp of *B. pertussis* sequence contained in pPX2557, and the next approximately 4.5 kb of the *B. pertussis* genome. A restriction map of this plasmid is shown in FIG. 2A. The solid lines in the map represent regions of pts included in pPX2557. The hatched regions represent vector plasmid pT3T7 DNA (a pUC-derived vector). The arrow marked "$kan^r$" denotes the site at which the kanamycin resistance marker was integrated into the chromosome of the strain (designated as PBCC554/pPX2579) used as a source of DNA for the cloned sequences. The open boxed region depicts approximately 4.5 kb of the cloned region present in pPX2871. FIG. 2B is a linear restriction map of the *B. pertussis* sequences cloned in pPX2871. The open boxed region depicts the region of the *B. pertussis* genome not previously cloned in pPX2557. The locations of the restriction sites within this region are approximate. The solid line at the beginning represents the region previously cloned in pPX2557 which encodes an incomplete open reading frame (SEQ ID NO: 12) homologous to a virB11 protein representative of a family of ATP-dependent translocases involved in transport of large proteins across the outer membrane. In both FIGS. 2A and 2B, the gene designated pstAB (SEQ ID NO: 2) for this plasmid does not contain the first 685 base pairs of the coding region.

At least six different open reading frames (or genes) are herein identified within the cloned sequences (FIG. 1). As described in greater detail in the following examples, this portion of the genome encodes gene products required for synthesis and extracellular export of holotoxin. The entire cloned region downstream of ptx beginning at base 4322 is designated pts, for pertussis toxin secretion genes. The first gene located in this region is designated ptsAB (SEQ ID NO: 2; (SEQ ID NO: 1). The start site of translation for ptsAB is located at base 4322, and the open reading frame continues to encode the 824 amino acid protein (SEQ ID NO: 3) until reaching a stop codon located at base 6794. ptsAB (SEQ ID NO: 2) is required for export of the assembled holotoxin from the periplasm and encodes a predicted amino acid sequence of which the first 523 amino acids are homologous to the predicted amino acid sequence of the virB4 gene product of *Agrobacterium tumefaciens* Ti plasmid (Ward, J. E., et al., *J. Bact.* 263(12):5804–5814 (1988)). The remaining C-terminal amino acids encode a predicted amino acid sequence that is homologous to the predicted amino acid sequence of the virB5 gene product of *A. tumefaciens* Ti plasmid.

Disruption of the ptsAB gene (SEQ ID NO: 2) results in a severe depletion of PT in the culture supernatant of the mutant strain. However, the periplasmic PT of the ptsAB mutant is assembled into a form that is qualitatively similar to the periplasmic PT of ptsAB wild type strains. These results indicate that the ptsAB gene product (SEQ ID NO: 3) is primarily involved in the secretion of assembled holotoxin from the periplasm across the outer membrane. Because the steady state level of ptxmRNA is not affected by the ptsAB mutation, the approximate 30-fold reduction in the level of PT synthesized by the ptsAB mutant is probably the consequence of post-transcriptional regulation. The ptsAB mutation does not appear to alter expression of other genes, including the bvg (vir) related functions involving fhaB (a gene required for expression of the virulence factor, filamentous hemagglutinin (FHA)) or cyaA (the gene encoding the virulence factor, hemolysis, an adenylate cyclase). The inability of the integrated pPX2833 plasmid containing ptsAB (FIG. 3) to completely restore the secretion defect created by disruption of ptsAB (in PBCC561) can be explained by inactivation of *B. pertussis* genes further downstream of ptsAB, due to vector DNA sequences, or by the presence of a partial protein product (synthesized from the disrupted ptsAB) that interferes with normal ptsAB function. Alternatively, the inability of pPX2833 to complement the ptsAB mutation can also indicate that the *B. pertussis* DNA contained on this plasmid is not integrated in the proper chromosomal context for cis regulated expression of ptsAB to occur (e.g., polar effects of the inserted vector DNA). The same ptsAB-containing fragment from pPX2833 can be used in plasmid pPX2777 to replace the disrupted chromosomal ptsAB region in the PBCC558 (ptsAB) mutant, without integration of vector DNA, and can completely restore wild type function.

Three additional mutations in the cloned region (identified by gene disruption experiments which localize the mutations to approximately 3 kb, 4 kb and 6 kb distal to ptsAB) (SEQ ID NO: 2) have PT export phenotypes similar to that of ptsAB, indicating that additional gene products encoded by these regions are required for export of holotoxin. DNA sequence analysis of these regions reveals that they contain open reading frames similar to those encoded by the Agrobacter Ti plasmid virB operon (Ward, J. E., Jr. et al., *Proc. Natl. Acad. Sci. USA* 88:9350–9354 (1991)). In particular, one of these *B. pertussis* mutations is localized to the extreme 3' end of the *B. pertussis* DNA clone, pPX2557. The DNA sequence of this region reveals an incomplete open reading frame containing homology to the virB11 and pule family of putative ATP dependent "secretion kinases," or translocases (Possot, O. et al., *Mol. Microbiol.* 5:95–101 (1992)). This open reading frame extends into a region of the chromosome now cloned and contained in pPX2871. If the similar genetic organization of the pts region and the Agrobacter vir region persists, then the sequences cloned in pPX2871 encode an open reading frame containing homology to the transcriptional regulatory virG proteins.

The hexameric pertussis toxin protein (PT) is a highly complex bacterial toxin of the A-B type structure. The enzymatically active A monomer (or S1 subunit) is associated with the B oligomer, which contains the S2, S3, S4, and S5 subunits complexed in a 1:1:2:1 molar ratio (Tamura, A., et al. *Biochemistry* 21:5516–5522 (1982). The genes for these subunits have been cloned and sequenced (Locht, C. and Keith, C. M., *Science* 232:1258–1264 (1986); Nicosia, A., et al. *Proc. Natl. Acad. Sci. USA* 83:4631–4635, (1986)). Each of the subunits is thought to be translated from the polycistronic ptx mRNA as a precursor protein containing signal sequences. The individual subunit precursors appear to be separately translocated across the cytoplasmic membrane into the periplasmic space where they are assembled into mature holotoxin. Transposon insertion in ptxS3 results in accumulation of the other subunits in the periplasmic space of the mutant strain (Marchitto, S. K., et al., *Infect. Immun.* 55:1309–1313 (1987); Nicosia, A. et al., *Infect. Immun.* 55:963–967 (1987)). The inability to detect any individual subunits in the culture medium of the ptxS3 insertion mutant indicates that the unassembled subunits are not transported across the outer membrane. Assembly and secretion of the B oligomer does not require an intact S1 subunit. Several different mutations in the S1 subunit (including carboxy terminal deletions which prevent association with the B oligomer) give rise to strains that secrete low levels of the B oligomer into the culture medium (Antoine, R. and Locht, C., *Infect. Immun.* 58:1518–1526 (1990); Pizza, M., et al., *J. Biol. Chem.* 265:17759–17763 (1990)).

Expression of ptx and other virulence factors is subject to regulation by the bvgA and bvgS gene products of *B. pertussis* (Roy, C. R. et al., *J. Bacteriol.* 271:6338–6344 (1989); Stibitz, S. et al., *Nature* 338:266–269 (1989)). These proteins act similarly to other two component signal transducing pathways (Miller, J. F. et al., *Science* 243:916–922 (1989)) to activate transcription of ptx, fhaB, cyaA, and other genes encoding virulence factors in *B. pertussis*. Expression of ptx has been shown to require factors in addition to the bvg gene products (Miller, J. F. et al., *J. Bacteriol.* 171:6345–6348 (1989)). However, the processing events and factors required for expression, assembly, and secretion of pertussis holotoxin remain to be elucidated.

The inability to obtain over expression of PT can be attributed largely to the complexity of the bvg dependent regulatory system, which controls transcription of the ptx operon (Gross, R. and Rappuoli, R., *Proc. Natl. Acad. Sci. USA* 85:3913–3917 (1988), as well as to the complexity of the multimeric holotoxin protein itself. The ptx operon is not transcribed in *E. coli* even when the BvgA transcriptional activator is present (Miller, J. F. et al., *J. Bacteriol.* 171:6345–6348 (1989). Although each of the individual PT subunits have been expressed individually in *E. coli* (using transcriptional or transcriptional and translational fusions) and then used for assembly of PT in vitro, the process is not readily amenable to large scale production. In addition, the in vitro assembled protein does not exhibit many of the same properties as the native holotoxin (Burnette, W. N. et al., *Bio/Technology* 6:699–705 (1988).

Attempts to express PT in the faster growing *B. parapertussis* and *B. bronchiseptica* species have been more successful (Lee, C. K. et al., *Infect. Immun.* 57:1413–1418 (1986). Both of these strains contain homologs of the ptx operon but the operon is not expressed because of several mutations in the promoter region (Arico, B. and R. Rappuoli, *J. Bacteriol.* 169:2847–2853 (1987). These species are able to express PT when an intact ptx operon is present. However, secretion or export of PT appears to be strain dependent and in most studies the majority of the toxin remains localized in the periplasm (Lee, C. K. et al., *Infect. Immun.* 57:1413–1418 (1989); Walker, M. J. et al., *Infect. Immun.* 59:4238–4248 (1991)). It is postulated that the inability of *B. parapertussis* and *B. bronchiseptica* to efficiently export holotoxin is due to the presence of extracellular transport systems in these organisms which differ from that of *B. pertussis* (Lee, C. K. et al., *Infect. Immun.* 57:1413–1418 (1989). For these and other reasons, large scale purifications of PT have depended on homologous *B. pertussis* host strains for expression of ptx.

The ability to use faster growing heterologous hosts (such as *E. coli* or *Bacillus subtilis*) or over expressing homologous or related hosts (such as *B. parapertussis* or *B. bronchiseptica*) would substantially reduce the amount of fermentor time required for PT production. The pts genes described herein can be used to enhance both expression and export of PT in recombinant homologous or heterologous hosts containing the ptx operon. For example, complementation of pts function in *B. bronchiseptica* or *B. parapertussis* can be obtained by supplying the pts operon on an integrating plasmid. Expression of pts genes can be further enhanced by fusing them with very active promoters (for example, the *E. coli* tac promoter). In addition, putative native pts homologs (such as those possibly occurring in *B. parapertussis* and *B. bronchiseptica*) can be deleted and replaced with *B. pertussis* pts genes, or with pts operatively linked to an active promoter. Another way to increase holotoxin production is to increase the copy number of the ptx genes, in conjunction with pts genes, in the recombinant homologous or heterologous strain. This can be done, for example, by providing multiple copies of ptx and pts on an autonomously replicating broad host range plasmid, for example, pRK290 ((Ditta, G. et al., *Proc. Natl. Acad. Sci. USA* 77:7347–7351 (1980)).

Recombinant strains of *B. pertussis* containing the *E. coli* tac promoter fused to the ptx operon export PT independently of some of the factors which normally regulate PT production (e.g., BvgA dependent functions), indicating that the number of factors required for production of PT in a heterologous host can be very limited, and therefore easily provided. Therefore, by using the cloned DNA herein described, homologous, heterologous or related strains can be generated which are capable of high levels of production of pertussis holotoxin. For example, broad host range plasmids containing ptx and pts operatively linked to one or more active promoters can be introduced into a related or heterologous host strain. ptx and pts can be present on one or more than one plasmid, and either or both of these operons can be made to integrate into the host genome using, for example, gene replacement techniques. One example of a construct useful for producing an over expressing strain is a $P_{tac}$-ptx pts fusion which contains both the ptx and pts operons operatively linked to the *E. coli* tac promoter. This construct can be supplied as an autonomously replicating plasmid, or it can be used to supplant a homologous region in the host cell's genome (for example, *B. parapertussis* or *B. bronchiseptica*) by gene replacement, (S. Stibitz et al., *Gene* 50:1765–1774 (1986)). Other approaches to producing holotoxin over expressing (or oversecreting) strains are further described in Examples 10 and 11. The ability to generate large quantities of holotoxin would make preparation of holotoxin for vaccine production both feasible and economical.

The invention will be further illustrated by the following nonlimiting examples.

EXAMPLE 1

Strains, Plasmids and Media

A brief description of the strains and plasmids described herein is presented in Table 1 and in FIG. 3. FIG. 3 depicts schematically the *B. pertussis* mutant strains and cloned mutant genomic sequences used in the following examples. The thick solid lines represent *B. pertussis* chromosomal regions or chromosomal sequences cloned in plasmid vectors. The plasmid vector sequences are not shown in this diagram and the *B. pertussis* regions cloned are positioned according to the chromosomal orientation. Open boxes depict deleted regions replaced by the kanamycin resistance (Kan$^r$) marker. The filled box (pPX2856) represents insertion of Kan$^r$ without deletion of cloned sequences; thick arrows represent intact open reading frames; Ptac depicts the *E. coli* tac promoter fusion in PBCC556; symbols for restriction sites are as follows R, EcoRI; Sm, SmaI; B, BamHI; K, KpnI; Bg, BglII.

*B. pertussis* strains are grown on solid Bordet-Gengou medium (BG; Difco Laboratories, Detroit, Mich.) containing 15% defibrinated horse blood (Crane Biologics, Syracuse, N.Y.) or in modified Stainer-Scholte liquid medium containing 0.1% 2,6-o-methyl-β-cyclodextrin (Teijin Limited, Tokyo, Japan) as described previously (Kimura, A. et al., *Infect. Immun.* 58:7–16 (1990)). Cultures grown under modulating conditions contain 50 mM MgSO$_4$ in both solid and liquid media. When antibiotics are included in either type of medium, they are added to the following concentrations: 50 µg/ml ampicillin, 25 µg/ml kanamycin, 200 µg/ml streptomycin, or 10 µg/ml tetracycline. Growth of liquid cultures is followed by measuring the optical density (OD) at 650 nm. Mid to late logarithmic phase cultures (OD=1.0 to 1.5) are used for most assays. *E. coli* strains are grown in LB medium (Sambrook, S. et al., 1989 Cold Spring Harbor Laboratory, Cold Spring Harbor, N. Y.) with ampicillin added to 100 µg/ml when required.

Plasmid Constructions and Genetic Manipulations

Restriction enzymes, T4 DNA ligase, T3 or T7 RNA polymerase, and other enzymes and nucleotides used for DNA or RNA manipulations are obtained from Boehringer Mannheim (Indianapolis, Ind.), Bethesda Research Laboratories Inc. (Bethesda, Md.), or New England Biolabs (Beverly, Mass.). DNA sequencing is carried out using an Applied Biosystems (Foster City, Calif.) model 370A DNA Sequencer. Computer searches of the Genbank International Nucleotide Sequence Databank (Intelligenetics Inc., Mountain View, Calif.) are done on a Macintosh IIci computer (Apple Computer, Cupertino, Calif.) using MacVector 3.5 software (International Biotechnologies Inc., New Haven Conn.). All other DNA manipulations are performed using standard conditions (J. Sambrook et al., 1989 Cold Spring Harbor Laboratory, Cold Spring Harbor, N.Y.).

Plasmid pPX2557 (Table 1 and FIG. 1) is obtained by selecting kanamycin resistant (Kan$^r$) recombinants in pUC19 from an EcoRV genomic digest of *B. pertussis* strain PBCC502 (similar to PBCC524, see FIG. 3) which contains a Kan$^r$ marker replacing the 5' region (KpnI to SmaI) of the ptx operon. The resulting pPX2557 plasmid contains 2.7 kb of the ptx operon and 8 kb of the adjacent 3' region. A 3.7 kb BglII fragment containing ptsA is subcloned from pPX2557 into the BamHI site of pUC18 to create pPX2833 (Table 1 and FIG. 3). The ptsAB gene in pPX2833 is disrupted by digestion with BamHI and insertion of the Kan$^r$ marker which replaces 438 bp of the ptsAB coding sequence in the resulting plasmid, pPX2834 (Table 1 and FIG. 3). Plasmid pPX2558 (Table 1 and FIG. 3) contains the ptsAB coding region, included as part of the 4.5 kb BamHI-SalI region from pPX2557 subcloned into pUC18. The C-terminal or B region of the ptsAB coding region contained in pPX2558 is interrupted by ligating the Kan$^r$ marker into the unique BglII to yield pPX2856 (Table 1 and FIG. 3). Plasmid pPX2777 is derived from pNO1523 (Pharmacia-LKB, Piscataway, N.J.) after destroying the EcoRI and HindIII sites of pNO1523 and ligating a DNA fragment, containing the pUC18 multiple cloning site and lacZ region, into the BamHI site of the modified pNO1523. The resulting plasmid (pPX2777, Table 1) permits blue/white screening for recombinants and the dominant, Str$^s$, rpsL allele facilitates the return of genes to Str$^r$ *B. pertussis*, similar to the method described for pRTP1 (S. Stibitz et al., *Gene* 50:1765–1774 (1986)). Plasmid pPX2857 (Table 1 and FIG. 3) is constructed by ligating the 3.7 kb BglII fragment, described above, into the unique BamHI site of pPX2777.

Plasmids are introduced into *B. pertussis* by electroporation using a BTX (San Diego, Calif.) Transfector 100 electroporator equipped with a 0.5 mm electrode and Power Plus module. Cells are prepared for electroporation by harvesting mid-logarithmic phase cultures (OD$_{650}$=0.8 to 1.0), washing them in ¼ the culture volume of 1 mM HEPES, pH7.2, and resuspending in 1/50 volume 1 mM HEPES, pH7.2, containing 10% glycerol, prior to storage at −70° C. (Zealey, G. et al., *FEMS Microbiol. Lett.* 50:123–126 (1988)). During electroporation the amplitude is set to obtain a pulse of 28–30 kv/cm. Cells are preincubated in liquid medium for 60 minutes at 37° C. and plated onto selective medium. For gene disruption experiments, pUC based vectors (which do not replicate in *B. pertussis*) are used and selection is for the Kan$^r$ marker used to replace or interrupt the gene of interest. Double recombination events (between the regions of the gene flanking both sides of the marker and the homologous chromosomal sequences) are scored by determining sensitivity to ampicillin. Plasmids derived from the pPX2777 vector are used to replace chromosomal sequences by streaking the Amp$^r$ transformants onto streptomycin plates followed by screening for the appropriate phenotype as described previously (Stibitz, S. et al., *Gene* 50:1765–1774 (1986)).

RNase Protection

RNA antisense probes are prepared from clones contained in pT3-T7 (Boehringer Mannheim) by transcription of the linearized templates in the presence of (α-$^{32}$P-GTP) (Amersham, Arlington Heights, Ill.). Total cellular RNA is isolated from mid logarithmic phase cells using a modification of the hot phenol method (von Gabain, A. et al., *Proc. Natl. Acad. Sci. USA* 80:653–657 (1983)). Fifty µg of RNA is incubated with 10$^5$ cpm of the radiolabelled probe in a final volume of 30 µl of hybridization buffer at 95° C. for 3 minutes prior to hybridization overnight at 58° C. Single stranded RNA is digested with RNase A and RNase T1 (Boehringer Mannheim, Indianapolis, Ind.) as described elsewhere (Kreig, P.A. and Melton, D.A., *Meth. Enzymol.* 155:397–415 (1987)). The protected RNA is fractionated on a denaturing 8% polyacrylamide gel along with MspI digested pBR322 radiolabelled size standards.

Immunochemical Assays

Colony immunoblots of *B. pertussis* are performed by standard procedures (Sambrook, S. et al., 1989 Cold Spring Harbor Laboratory, Cold Spring Harbor, N.Y.) after growing cells on nitrocellulose filters (BA85, Schleicher & Schuell, Keene, N. H.) for 2–3 days. The presence of PT is detected using a goat anti-pertussis toxin (PT) antibody fraction and horse radish peroxidase (HRP) conjugated rabbit anti-goat antibody (Zymed, San Francisco, Calif.). Positive colonies are visualized by incubation with 4-chloro-1-naphthol and hydrogen peroxide. PT is adsorbed from culture supernatants onto fetuin agarose (Sigma Chemical Co., St. Louis, Mo.) as previously described (Kimura, A. et al., Infect. Immun. 58:7–16 (1990)). The adsorbed PT is analyzed by SDS-polyacrylamide electrophoresis (Laemmli, U.K., Nature 227:680–685 (1970)) using 16% SDS-polyacrylamide gels. For Western analysis, whole cell lysates are resolved on 16% SDS-polyacrylamide gels, electroblotted onto nitrocellulose (BA55, Schleicher & Schuell) and probed using goat anti-PT and HRP rabbit anti-goat antibody as described above. Volumes of samples used for SDS-polyacrylamide electrophoresis and Western analyses are normalized to the culture OD. Hemagglutination assays are conducted as previously described (Sato, Y. et al., Infect. Immun. 41:313–320 (1983)) using a 1% suspension of washed goose red blood cells (Crane Biologics, Syracuse, N.Y.).

The level of toxin in the culture supernatant and in the periplasmic space is determined by an antigen capture ELISA. The integrity of the toxin is assessed by ELISA based assays in which the binding ability of the toxin to either fetuin or the PT receptor in Chinese hamster cells (CHO) is measured. Microtiter plates are coated with either goat polyclonal antibodies to PT for the antigen capture ELISA, fetuin for the fetuin binding ELISA, or CHO cell cytoplasmic membranes for the CHO membrane binding ELISA. The CHO cell membranes are isolated (Brennan, M. J., et al., J. Biol. Chem. 263:4895–4899 (1988)) from CHO-K1 cells or from CHO-15B cells. Because the receptor in the ricin-resistant CHO-15B cells is defective and can no longer bind PT (Locht, C. et al., Infect. Immun. 55:2546–2553 (1987)), the difference in the extent of PT binding to the CHO-K1 membranes and to the CHO-15B membranes is taken to represent the specific binding of PT to the receptor.

Unless otherwise specified, the following steps for ELISA analyses are performed at 37° C. for 1 hour. Coated plates are blocked with 2% bovine serum albumin (BSA). The culture supernatant as well as the periplasmic fraction are serially diluted and added to the plates for incubation. The bound toxin is probed with a mouse polyclonal serum to PT followed by alkaline phosphatase conjugated goat F(ab')2 anti-mouse immunoglobulins (Tago Inc., Burlingame, Calif.). The plates are then developed with 1 mg/ml p-nitrophenyl phosphate for 30 minutes at room temperature and the OD at 410 nm is measured.

In each ELISA, purified PT is used to establish a standard curve. The specific binding activity of PT, defined as OD/µg protein, is derived from the linear portion of a plot of net OD versus PT concentration. Based on these standard curves, the toxin concentration of the test samples is calculated. The detection limit is from 1 to 10 ng/ml for the antigen capture ELISA, from 8 to 80 ng/ml for the fetuin binding ELISA, and from 3 to 30 ng/ml for the CHO receptor binding ELISA.

The periplasmic fractions used in the above-described ELISAs are prepared using polymixin B (Sigma, St. Louis, Mo.) treatment of concentrated whole cells (Pizza, M. et al., J. Biol. Chem. 265:17759–17763 (1990)). The level of toxin recovered in these fractions is normalized to the relative yield of the periplasmic material as estimated by the β-lactamase activity present in the periplasmic and cellular fractions of PBCC561 and other Amp$^r$ control strains.

EXAMPLE 2

Identification of B. pertussis toxin secretion mutants

First, the identity of the pts region was discovered upon construction of a ptx deletion strain. A 4.6 kb EcoRI-BamHI B. pertussis chromosomal region carrying the entire ptx operon and 1.3 kb of 3' flanking sequence (FIG. 3) is replaced with the Kan$^r$ marker by homologous recombination with the flanking DNA sequences present on pPX2561 (FIG. 3). Gene replacement is verified by Southern hybridization analysis. All of the isolates remain hemolytic and produce filamentous hemagglutinin (FHA) (measured by hemagglutination) and 69K outer membrane protein (OMP) (or pertactin (Roberts, M. et al., Mol. Microbiol. 5:1393–1404 (1991)), as determined by Western analysis) upon repeated subculturing. One of the isolates (PBCC537, FIG. 3) is used as a host to examine the expression of PT from plasmid copies of the ptx operon.

After electroporation of PBCC537 with pRK290 based plasmids (Ditta, G. et al., Proc. Natl. Acad. Sci. USA 77:7347–7351 (1980)) that are capable of replicating in B. pertussis and contain an intact ptx operon (for example pPX2727, FIG. 3), Amp$^r$ transformants are screened for toxin production by colony immunoblot. All of the hemolytic colonies tested also produce toxin protein as judged by a positive reaction on colony immunoblots. Positive colonies are further tested for the presence of toxin in the culture supernatant by growing small scale liquid cultures and testing the supernatants for toxin by fetuin binding ELISA. On the basis of these tests, all of the isolates tested are unable to secrete holotoxin (or the B-oligomer) into the culture medium. The inability of the PBCC537 transformed strains to secrete toxin is not due to a defect in the plasmids or plasmid borne ptx gene; toxin expressed from the same plasmids is secreted from other B. pertussis host strains (PBCC524 or similar hosts) that are deleted only for the 5' region of the ptx operon. In PBCC537 reconstitution with the ptx gene was not sufficient for PT holotoxin secretion. Therefore, regions 3' to ptx are involved in the secretion of the toxin.

EXAMPLE 3

Identification and sequence analysis of ptsAB

Computer analysis of the DNA sequence deleted in PBCC537 reveals an incomplete open reading frame (ORF) that starts 697 bp downstream from the end of the ptxS3 coding sequence and extends beyond the end of the published sequence (Nicosia, A. et al., Proc. Natl. Acad. Sci. USA 83:4631–4635 (1986)). A search of Genbank shows that the predicted product of this ORF is homologous to the predicted virB4 gene product which is thought to be part of a multi-protein complex involved in transport of the Ti plasmid DNA across the cell envelope of Agrobacter tumefaciens (Ward, J. E., Jr. et al., Proc. Natl. Acad. Sci. USA 88:9350–9354 (1991)). Additional DNA sequencing of the ptx 3' ORF contained in pPX2833 reveals a predicted protein sequence that is homologous (29% identity) to virB4 throughout the first 523 amino acids. This region is referred to as the pts (pertussis toxin secretion) locus and this specific ORF is referred to as the ptsA region of ptsAB.

EXAMPLE 4

Characterization of ptsAB function in holotoxin assembly or secretion

To more clearly demonstrate the requirement of ptsAB in the assembly or secretion of PT, the ptsAB is subcloned as a 3.7 kb BglII DNA fragment (pPX2833, FIG. 3), and then an internal BamHI-BamHI fragment of the putative gene is replaced with a marker for kanamycin resistance. The disrupted ptsAB gene contained on pPX2834 (Table 1 and FIG. 3) is used to replace the intact chromosomal copy of ptsAB (SEQ ID NO: 2) by electroporation of PBCC554 (Table 1 and FIG. 3) followed by selection on kanamycin and screening for $Amp^s$, hemolytic colonies. All of the hemolytic, $Kan^r$, $Amp^s$ colonies test positive for PT by colony immunoblot. Twelve isolates are further screened for secretion of PT by growing small scale cultures and testing the culture supernatants for hemagglutination activity. All twelve are negative for any hemagglutination activity. One of the isolates is designated PBCC558 and saved for further characterization.

Attempts to completion toxin assembly or secretion defect created in PBCC558 by integrating the copy of ptsAB using pPX2833 yield the following results: 15 of 18 hemolytic, $Amp^r$ transformants tested remain positive by colony immunoblot, but only marginal hemagglutination activity (titers of 1:2 to 1:4) can be detected in the culture supernatants. One of these transformants is designated PBCC561 (Table 1). Subcloning the same region into pPX2777 (Table 1) demonstrates that the assembly or secretion defect can be completely restored by the 3.7 kb BglII fragment. The resulting plasmid, pPX2857 (Table 1) facilitates replacement of the disrupted chromosomal region of PBCC558 without integration of vector sequences. Two isolates of the appropriate phenotype ($Amp^s$, $Kan^s$, $Str^r$ and hemolytic) contain levels of hemagglutination activity in culture supernatants that are identical to the PBCC554 parental strain. One of the isolates is PBCC563 (Table 1).

EXAMPLE 5

Identification and sequence analysis of ptsB region of ptsAB

DNA sequencing of the regions flanking the site of the BglII insertion in pPX2856 reveals that insertion of the $Kan^r$ marker interrupts a second portion of the open reading frame (ORF). This second portion which extends from 5909–6867 bp codes for a polypeptide which is 33% identical to the predicted virB5 gene product of *A. tumefaciens*. This region is designated ptsB.

EXAMPLE 6

Characterization of pts function in expression, assembly and secretion of holotoxin SDS-PAGE and Western analysis of fetuin bound material recovered from culture supernatants from PBCC558 and PBCC561 allows for characterization of the nature of the defects in these mutants by assaying for the presence of secreted holotoxin. The results of SDS-PAGE show that PBCC558 and PBCC561 are depleted for extra-cellular PT in a form capable of binding fetuin and that no detectable PT is recovered from PBCC562 (a ptx promoter mutation). The goat anti-PT polyclonal antibody, which detects primarily the S1 subunit of PT, is used for Western analysis of the fetuin absorbed fractions from the above strains. The presence of the S1 subunit is readily detected in PBCC554 and PBCC563 and is present at lower levels in the two ptsA mutant strains PBCC558 and PBCC561. The presence of S1 in the fetuin absorbed fraction from the two mutant strains indicates that the low level of PT secreted by these strains is in the form of holotoxin, as opposed to only the B-oligomer, which also binds to fetuin. A faint band migrating slightly below the S1 protein is detected by polyclonal antisera in culture supernatants from PBCC562 is also detected in the fetuin absorbed fraction and whole cell lysates of other ptx deletion strains. This band is therefore most likely due to a low level of a cross reactive protein. The presence of wild type levels of PT and S1 recovered from PBCC563 also shows that repair of the disrupted ptsAB (SEQ ID NO:2) in PBCC563 restores the capacity to secrete wild type levels of PT holotoxin. Western analyses of whole cell lysates of the different strains show that the S1 subunit is detected in lysates of all strains except the PBCC562 ptx mutant.

The observation that integration of pPX2557 and 2558 and other subclones of the pts region eliminates PT export indicates that these genes of the pts locus are necessary for the secretion of the holotoxin.

EXAMPLE 7

Characterization of the ptsAB mutant phenotype—ptsAB mutant is secretion defective Assays that permit estimation of the amount of PT protein present relative to the amount of functional PT capable of binding to either fetuin coated microtiter plates or CHO cell membrane coated microtiter plates are used to determine whether the defect present in PBCC558 is due to the failure of the strain to assemble the toxin subunits into a form that can bind fetuin or CHO cell membranes, or if the defect is due to an impaired capacity to secrete the assembled holotoxin. The three different assays provide a range of values for the estimated absolute amount of PT present in culture supenatants (Table 2). The values obtained by the fetuin and CHO membrane ELISAs are 1.3 to 1.4 fold higher, respectively, than those obtained by antigen capture ELISA of PBCC554 culture supernatant. However, it is clear that PBCC554 (which serves as a wild type control) contains only a small fraction (less than 5%) of the total PT protein (extracellular plus periplasmic) in the periplasmic fraction, as detected by the antigen capture ELISA, and that the bulk of the PT is recovered in the culture supernatant. The ptsAB mutant, PBCC558, is severely reduced in the total amount of PT and this reduction can be attributed almost entirely to the lack of extracellular PT (Table 2). The small amount (~3% of wild type level) of extracellular PT that is detected by antigen capture ELISA of PBCC558 culture supernatants also appears functional in the fetuin and CHO cell membrane binding ELISAs (Table 2). The periplasmic PT from PBCC558 does not appear significantly different than the periplasmic PT from PBCC554; about the same amount of PT is recovered from the periplasmic fraction from both strains and approximately the same fraction (0.4–0.5x) is detected by the fetuin binding and CHO binding assays (Table 2).

These results indicate that the defect conferred by the ptsAB mutation present in PBCC558 is not a consequence of defective assembly of PT, but is due to the inability of the mutant strain to secrete the assembled PT holotoxin or B-oligomer. The ELISA results also indicate that the integrated copy of pPX2833 (which contains an intact ptsA region) in PBCC561 does not result in any significant increase in the amount of secreted PT. PBCC562 lacks any detectable PT in either the periplasmic or extracellular fraction (Table 2). Similar assays have shown that PBCC563 is very similar to the original parental strain (PBCC554) with respect to the amount of functional PT present in both the periplasm and culture supernatant.

EXAMPLE 8

Assay for the ptsAB transcriptional start site

Initial identification of the transcription start site for the mRNA encoding ptsAB (SEQ ID NO:3) uses an antisense RNA probe homologous to a region 89 bp before the predicted translation start site and including 370 bp of the complementary coding sequence. Using this probe for RNase protection of the mRNA synthesized by the wild type (Tohama) strain grown under non-modulating conditions reveals that the entire length of the probe is protected from RNase digestion, indicating that the transcriptional start site for ptsAB occurs upstream of the region probed. An RNA antisense probe extending further upstream from the translation start (−90 to −698) of ptsAB (SEQ ID NO:2) is used to hybridize to RNA from the wild type strain grown under modulating (+MgSO$_4$) and non-modulating (−MgSO$_4$) conditions. The results of this experiment show that the probe is protected only when used to hybridize to RNA from the wild type strain grown under non-modulating conditions. The estimated size of this band (~600 nt) is the size expected if the entire length of the probe, minus −160 nt corresponding to vector sequences, is protected from RNase digestion. These results indicate that transcription of ptsAB is regulated by the presence of MgSO$_4$, and that initiation of transcription occurs upstream of the region probed (i.e., 5' of the end of ptxS3).

EXAMPLE 9

The ptsAB mutant displays wild type levels of ptx mRNA

RNA from the different mutants is hybridized to an RNA antisense probe overlapping the −167 to +327 region of ptx transcription initiation site in order to determine if the ptsAB mutation alters transcription of ptx. Results from this experiment show that the RNA from Tohama protects a region of the probe (corresponding to approximately 327 nt) expected if transcription initiates at the published transcription initiation site (Nicosia, A. et al., Proc. Natl. Acad. Sci. USA 83:4631–4635 (1986)). RNA from PBCC554 protects two regions of the probe corresponding to ~150 nt and ~120 nt. The 150 nt band is expected if transcription of ptx starts at the same transcription initiation site and extends through the R9K mutation present in PBCC554. The 120 nt band is the expected digestion product corresponding to the distance from the W261 mutation to the end of the probe. For each of these mutations, the three base pair mismatch of the RNA duplex formed by hybridization of the wild type sequence of the probe with mRNA corresponding to the mutated regions in PBCC554 (and its derivatives), results in digestion by RNase to yield the observed pattern. RNA from PBCC558, PBCC561 and PBCC563 also protects the same levels and regions of the probe from RNase digestion. However, PBCC562 lacks any detectable ptxmRNA (as predicted for a ptx promoter mutant strain). These results demonstrate that the translation of ptx mRNA is also dependent upon ptsAB function.

EXAMPLE 10 pts gene products can facilitate over expression of PT in homologous expression systems Our results show that in wild type B. pertussis, ptsAB (SEQ ID NO:2) is subject to virulence modulation and is regulated at the transcriptional level in a manner similar to the other bvg regulated genes in B. pertussis. However, when transcription of ptx is uncoupled from bvg regulation by fusion to P$_{tac}$ as in PBCC556 (Table 1 and FIG. 3), expression of pts secretion function also becomes independent of bvg and holotoxin is secreted even when MgSO$_4$ is included in the growth medium. The inability to detect the 5' end of the ptsAB mRNA within almost 700 bp of the translation initiation codon and the observation that transcription of ptsAB appears to be regulated by modulation growth conditions indicate that expression of ptsAB may be regulated by ptx. We have also shown that ptx promoter deletion strains (e.g., PBCC562) do not synthesize pts mRNA.

Characterization of the ptsAB mutant demonstrates that enhanced secretion of PT from the periplasm provides a net increase in the recovery of PT in culture supernatants. Thus, increasing the amount or activity of ptx gene products and similar gene products can itself result in enhanced recovery of PT, or can result in increased levels of PT when used in conjunction with one or more of the approaches described previously (e.g., increased ptx gene dosage, use of alternate transcriptional/translational signals, or improved activity of transcriptional activators such as BvgA). This approach to increasing PT expression and secretion is supported by a strain (designated PBCC566) containing the E. coli tac promoter fused to the translation initiation site of ptx. This strain exhibits levels of PT in the culture supernatant that are increased above wild type levels.

One of the advantages of utilizing the heterologous Bordetella species, B. parapertussis or B. bronchiseptica for expression of PT is that the faster growth of these species would substantially reduce the amount of fermentor time required (effectively increasing the yield of PT). One of the limitations of this approach is that even when these species are supplied with an intact ptx operon, they do not consistently or efficiently export PT into the culture supernatant. This problem is overcome by using the pts genes of B. pertussis to enhance expression and export of PT in recombinant B. parapertussis or B. bronchiseptica containing the pts operon. Complementation of pts functions in these species can be obtained by supplying the ptx-pts operon (or promoter fusions to pts) on an integrating plasmid. In the alternative, putative pts (pseudo- gene or homologs) found in the cells as obtained can be deleted and replaced with the B. pertussis genes. Many of the same manipulations that enhance expression of PT in B. pertussis (e.g., promoter fusions, increased ptx gene dosage, etc.) will function to enhance expression of PT in other recombinant Bordetella species when used in conjunction with pts complementation.

Recombinant strains of B. pertussis containing the E. coli tac promoter fused to the ptx operon export wild type levels of PT even in the presence of a modulating agent (MgSO$_4$) in the growth medium. Therefore, the presence of the tac promoter is sufficient to bypass any BvgA requirement for export of PT.

EXAMPLE 11 pts gene products can facilitate expression of PT in heterolgous expression systems One approach to obtaining expression and export of PT in heterologous systems which lack the Type II secretory pathway (Salmond, G. P. C. and P. J. Reeves, TIBS 18:7–12 (1993)) (used for export of PT by B. pertussis), is to supply the heterologous host (e.g., E. coli) with the export factors encoded by the pts operon (in addition to the ptx operon) on one or more plasmids. The feasibility of this approach is supported by previous work showing that Type II secretory pathways have been functionally reconstituted in E. coli (Possot, O. et al., Mol. Microbiol. 5:95–101 (1992); Cussac, V. et al., Microb. Ecol. Health Dis. 4:5139 (1991)). P$_{tac}$-ptx pts fusions are sufficient for expression and export of PT in a heterologous system lacking the Type II secretory pathway, or additional promoter fusions to other pts encoded factors may be required. In the event that other pts encoded factors are required, clones containing the P$_{tac}$-ptx fusions contiguous with the entire pts operon are constructed. Although it is unlikely, in the event that reconstitution of export requires Bvg dependent functions, the host can be co-transformed with bvgAS containing plasmids constructed for this purpose.

We obtained several clones of the ptx-pts region from the P$_{tac}$ ptx-pts fusion strain, PBCC556, by first screening an E. coli library (constructed in the commercially available "SuperCosI" system) for the presence of the ptx-pts region by virtue of the homology to the 3.7 kb BglII region present in pPX2833 as described above. Six positive colonies obtained by stringent hybridization (0.1×SSC 0.2% SDS @ 65° C.) were then tested for the presence of PT cross reacting proteins by colony blot analysis using an anti-S1, S2 and S4 monoclonal antibody mixture as described above. All six clones, positive by colony hybridization, were also positive by the colony immunoblot assay. The positive clones were then assayed for the ability to express PT in whole cell lysates as determined by Western analysis.

We purified this cloned plasmid DNA from the six clones and used it to transform a protease deficient (ompT ionA) BL21 E.coli expression host strains and assayed the transformed strains for the ability to express and export PT under different physiological conditions. Stationary phase cultures transformed with one of the clones (pPX2879, which contains an intact ptx-pts region) were capable of producing a substantial amount of PT cross reacting protein in the culture supernatant. The material recovered from the supernatant was shown to be in the form of holotoxin by subjecting the material present in the supernatant to fetuin-agarose affinity chromatography. As described previously, (Tamura, M. et al., *Biochemistry,* 21:5516–5522 (1982) and Chong P. et al., *Biochem. Cell Biol.,* 67:387–391 (1989)), the S1 subunit of the holotoxin can be recovered from such an affinity column (which binds both the B-subunit and the holotoxin) only if the holotoxin is bound to the affinity matrix to begin with. The culture supernatants of the BL21 pPX2879 *E. coli* transformants contain PT which can be adsorbed and eluted from fetuin-agarose and is in the form of PT holotoxin as detected using monoclonal anti-S1, S2 and S4 mixture for Western analysis.

Cloning the ptx and pts operons (containing promoter fusions to bypass BvgA function) on broad host range plasmids (Ditta, G. et al., *Proc. Natl. Acad. Sci. USA* 77:7347–7351 (1980) allows for screening a large number of alternate hosts for the ability to export PT. The advantage in utilizing other bacterial species for export of PT is that many of them may contain similar "Type II-like" secretory factors that may more efficiently complement the pts encoded factors of *B. pertussis.*

Bioloqical Deposits

PBCC558, DH5α, pPX2871 and DH5α, pPX2557 were deposited under the terms of the Budapest Treaty with the American Type Culture Collection (ATCC), 12301 Parklawn Drive, Rockville, Md. 20852 on Mar. 12, 1993 and have been assigned ATCC Accession Numbers 55402, 69255 and 69256, respectively. All restrictions upon the availability to the public of the deposited material will be irrevocably removed upon granting of a patent on this application. These deposits will be maintained in a public depository for a period of at least 30 years from the date of deposit or for the enforceable life of the patent or for the period of five years after the date of the most recent request for the furnishing of a sample of the biological material, whichever is longer. The deposits will be replaced if they should become nonviable or nonreplicable.

Those skilled in the art will recognize, or be able to ascertain using no more than routine experimentation, many equivalents to the specific embodiments described herein. Such equivalents are intended to be encompassed by the following claims.

TABLE 1

Description of Bacterial Strains and Plasmids

| *B. pertussis* Strains[a] | Description |
|---|---|
| PBCC524 | ptxΔ::$Kan^r$ ($Kan^r$ marker replacing ptx 5' region) |
| PBCC526 | spontaneous $Str^r$ isolate of Tohama wild type |
| PBCC537 | ptxΔ4::$Kan^r$ ($Kan^r$ marker replacing entire ptx) |
| PBCC554 | ptxS1-9K, $261^r$,$Str^r$,fhaB::$Tet^r$ (fhaB* derivative of PBCC526 containing a double mutation in S1) |
| PBCC556 | $Str^r$, fhaB::$Tet^r$,Φ ($P_{tac}$-ptx)(*E. coli* tac promoter fused to ptx coding region) |
| PBCC558 | PBCC554 containing ΔptsAB::$Kan^r$ |
| PBCC561 | PBCC558 with integrated $Amp^r$ pPX2833 |
| PBCC562 | PBCC554 containing ptx::$Kan^r$ |
| PBCC563 | PBCC558 with ΔptsAB::$Kan^r$ replaced with wild type sequences |
| Plasmids[c] | |
| pPX2557 | genomic clone in pUC18 containing 8 kb 3' of ptx |
| pPX2558 | 4.5 kb BamHI-SalI subclone from pPX2557 containing ptsAB (SEQ ID NO: 2) in pUC18 |
| pPX2561 | $Kan^r$ replacing 4.6 kb EcoRI-BamHI region of ptx and ptsAB (SEQ ID NO: 2) |
| pPX2727 | ptx operon contained on pRK290 derivative |
| pPX2777 | pN01523 ($Str^3$) derivative |
| pPX2833 | 3.7 kb BglII subclone from pPX2557 containing ptsAB (SEQ ID NO 2) in pUC18 |
| pPX2834 | ΔptsAB::$Kan^r$ ($Kan^r$ insert in ptsA region of pPX2833) |
| pPX2856 | ptsAB::$Kan^r$ ($Kan^r$ insert in ptsB region of pPX2558) |
| pPX2857 | 3.76 kb BglII subclone from pPX2557 containing ptsAB (SEQ ID NO: 2) in pPX2777 |

[a]All *B. pertussis* strains listed are hemolytic (Hly+)

[b]PBCC554 and derived strains contain a double mutation (ptxS1-9K,261) in the ptxS1 gene encoding for $Arg^9$ to Lys and Trp26 to Ile.

[c]All plasmids except pPX2727 and pPX2777 are pUC based vectors.

TABLE 2

Comparisons of PT in culture supernatants and periplasmic fractions from *B. pertussis* strains containing a mutation in ptsAB (SEQ ID NO: 2).

| | | | ELISA | | |
|---|---|---|---|---|---|
| Strain | $OD_{650}$ | Fraction | Antigen[b] | Fetuin[c] | CHO[c] |
| 554 | 1.52 | supernatant | 96.4 | 1.3 × (125) | 1.4 × (135) |
| | | periplasm[a] | 3.3 | 0.4 × (1.3) | 0.4 × (1.3) |
| 558 | 1.30 | supernatant | 3.6 | 0.8 × (2.9) | 0.9 × (3.2) |
| (ptsAB) | | periplasm | 2.8 | 0.5 × (1.4) | 0.4 × (1.1) |
| 561 | 1.19 | supernatant | 2.8 | 1.0 × (2.8) | 0.8 × (2.2) |
| (ptsAB) | | periplasm | 3.6 | 0.3 × (1.1) | 0.3 × (1.1) |
| 562 | 1.46 | supernatant | <0.001 | <0.008 | <0.003 |
| (ptx) | | periplasm | <0.001 | <0.008 | <0.003 |

[a]Values listed for the periplasmic fractions from each strain are normalized to the percentage of the fraction recovered.

[b]The values listed represent μg of PT from 50 ml culture.

[c]The values listed are fractions or multiples of the amount of PT detected by the antigen capture ELISA. Numbers in parenthesis represent μg of PT from 50 ml culture. the values listed for PBCC562 are below the indicated limit of detection (g/ml culture) of the respective assays.

We claim:

1. Isolated DNA comprising the nucleotide sequences as shown in SEQ ID NO:1, and which encodes gene products which facilitate extracellular export of *Borderella pertussis* toxin, or a portion of SEQ ID NO:1 which encodes a gene product which facilitates extracellular export of *Borderella pertussis* toxin, selected from the group consisting of ptsAB (SEQ ID NO:3), ptsC (SEQ ID NO:5), ptsD (SEQ ID NO:7), ptsE (SEQ ID NO:9), ptsF (SEQ ID NO:11) and ptsG (SEQ ID NO:13).

2. A plasmid construct containing the DNA of claim 1.

3. A plasmid construct comprising DNA comprising SEQ ID NO:1 and encoding gene products which facilitate secretion of *Bordetella pertussis* holotoxin.

4. A plasmid construct of claim 3 designated pPX2557, ATCC Deposit No. 69256.

5. Isolated DNA consisting of the *Bordetella pertussis* sequences cloned in plasmid pPX2557, ATCC Deposit No. 69256.

6. A plasmid construct comprising an approximately 12.5 kb seqment of DNA which is identical in nucleotide sequence to a region of *Bordetella pertussis* genome which maps from approximately 5 kb to approximately 17.5 kb 3' of the beginning of ptx.

7. A plasmid construct of claim 6 designated pPX2871, ATCC Deposit No. 69255.

8. Isolated DNA consisting of the *Bordetella pertussis* sequences cloned in plasmid pPX2871, ATCC Deposit No. 69255.

9. A Bordetella host bacterium transformed with the plasmid of claim 3.

10. A Borderella host bacterium transformed with the plasmid of claim 6.

11. A host bacterium transformed with the plasmid construct of claim 3 wherein the bacterium is selected from the group consisting of *Bordetella pertussis*, *Borderella parapertussis*, *Borderella bronchiseptica*, and *Escherichia coli*.

12. A host bacterium transformed with the plasmid construct of claim 6 wherein the bacterium is selected from the group consisting of *Bordetella pertussis, Borderella parapertussis, Bordetella bronchiseptica*, and *Escherichia coli*.

13. A method for producing secreted pertussis holotoxin in a Borderella or *Escherichia coli* host, said method comprising the steps of:
    a) constructing a plasmid comprising ptx and pts operatively linked to an active promoter;
    b) introducing the plasmid into the host; and
    c) maintaining the host under conditions appropriate for expression of ptx and pts and secretion of pertussis holotoxin.

14. Isolated DNA comprising the nucleotide sequence in SEQ ID NO:1, and which encodes gene products which facilitate extracellular export of *Bordetella pertussis* toxin.

15. Isolated DNA comprising the nucleotide sequence in SEQ ID NO:1, or a portion thereof, wherein said nucleotide sequence or portion thereof encodes at least one gene product which facilitates extracellular export of *Borderella pertussis* toxin.

16. An isolated nucleic acid which encodes a gene product which facilitates extracellular export of *Borderella pertussis* toxin, wherein the gene product is selected from the group consisting of ptsAB (SEQ ID NO:3), ptsC (SEQ ID NO:5), ptsD (SEQ ID NO:7), ptsE (SEQ ID NO:9), ptsF (SEQ ID NO:11) or ptsG (SEQ ID NO:13).

17. A method for producing secreted pertussis holotoxin, said method comprising the steps of:
    a) constructing a plasmid comprising ptx and pts, each operatively linked to an active promoter;
    b) introducing the plasmid into an *Escherichia coli* or a Borderella host; and
    c) maintaining the host under conditions appropriate for expression of ptx and pts and secretion of pertussis holotoxin.

18. A method for producing secreted pertussis holotoxin, comprising maintaining under conditions appropriate for expression and secretion of pertussis holotoxin, an *Escherichia coli* or a Borderella host transformed with one or more vectors comprising ptx and pts operatively linked to appropriate gene expression control sequences.

* * * * *